US012113998B2

(12) United States Patent
Bae et al.

(10) Patent No.: US 12,113,998 B2
(45) Date of Patent: Oct. 8, 2024

(54) NO REFERENCE IMAGE QUALITY ASSESSMENT BASED DECODER SIDE INTRA PREDICTION

(71) Applicant: Ofinno, LLC, Reston, VA (US)

(72) Inventors: Tae Meon Bae, McLean, VA (US); Esmael Hejazi Dinan, McLean, VA (US); Kalyan Goswami, Reston, VA (US)

(73) Assignee: Ofinno, LLC, Reston, VA (US)

( * ) Notice: Subject to any disclaimer, the term of this patent is extended or adjusted under 35 U.S.C. 154(b) by 0 days.

(21) Appl. No.: 17/525,606

(22) Filed: Nov. 12, 2021

(65) Prior Publication Data
US 2022/0159281 A1    May 19, 2022

Related U.S. Application Data

(60) Provisional application No. 63/113,230, filed on Nov. 13, 2020.

(51) Int. Cl.
*H04N 19/44*        (2014.01)
*C12N 1/16*         (2006.01)
(Continued)

(52) U.S. Cl.
CPC ............ *H04N 19/44* (2014.11); *C12N 1/165* (2021.05); *C12N 15/815* (2013.01); *H04N 19/11* (2014.11);
(Continued)

(58) Field of Classification Search
CPC ...... H04N 19/44; H04N 19/11; H04N 19/159; H04N 19/176; H04N 19/18; H04N 19/154; H04N 19/463
See application file for complete search history.

(56) References Cited

U.S. PATENT DOCUMENTS

| 2014/0254680 A1* | 9/2014 | Ho ....................... H04N 19/117 375/240.16 |
| 2017/0264914 A1* | 9/2017 | Agyo ................... H04N 19/176 |

(Continued)

FOREIGN PATENT DOCUMENTS

| CN | 101919255 A | * 12/2010 | ........... H04N 19/105 |
| FR | 3029055 A1 | * 5/2016 | ........... H04N 19/109 |

OTHER PUBLICATIONS

Bosse et al.; A Deep Neural Network for Image Quality Assessment; 2016 IEEE International Conference on Image Processing (ICIP); Sep. 25-28, 2016; pp. 3773-3777; IEEE; Phoenix, AZ, USA.
(Continued)

*Primary Examiner* — Dramos Kalapodas
(74) *Attorney, Agent, or Firm* — Shan He; Kavon Nasabzadeh; Jacob L. Mangan

(57) ABSTRACT

A decoder may receive, for a block, an indication of decoder-side-prediction and a reconstructed residual block from a bit stream. The decoder may generate, for each respective intra prediction mode of a plurality of intra prediction modes, a reconstructed block based on: a prediction block generated for the respective intra prediction mode; and the reconstructed residual block. The decoder may determine a selected prediction mode, from the plurality of intra prediction modes, for the block based on a visual quality of each of the reconstructed blocks. The decoder may decode the block based on the indication of the decoder-side-prediction and the selected prediction mode.

20 Claims, 24 Drawing Sheets

(51) Int. Cl.
  *C12N 15/81* (2006.01)
  *H04N 19/11* (2014.01)
  *H04N 19/159* (2014.01)
  *H04N 19/176* (2014.01)
  *H04N 19/18* (2014.01)

(52) U.S. Cl.
  CPC ......... *H04N 19/159* (2014.11); *H04N 19/176* (2014.11); *H04N 19/18* (2014.11)

(56) References Cited

U.S. PATENT DOCUMENTS

| | | | |
|---|---|---|---|
| 2019/0052888 A1* | 2/2019 | Xu | H04N 19/46 |
| 2020/0413068 A1* | 12/2020 | Xu | H04N 19/593 |
| 2021/0211739 A1* | 7/2021 | Andreopoulos | H04N 19/103 |
| 2022/0078448 A1* | 3/2022 | Xu | H04N 19/134 |

OTHER PUBLICATIONS

Ghadiyaram et al.; A No-Reference Video Quality Predictor for Compression and Scaling Artifacts; 2017 IEEE International Conference on Image Processing (ICIP); Sep. 17-20, 2017; IEEE; Beijing, China.

Ma et al.; A novel non-reference image quality assessment algorithm; 2017 IEEE 2nd Information Technology, Networking, Electronic and Automation Control Conference (ITNEC); Dec. 15-17, 2017; pp. 560-566; IEEE; Chengdu, China.

Kim et al.; Deep CNN-Based Blind Image Quality Predictor, IEEE Transactions on Neural Networks and Learning Systems; Jun. 12, 2018; IEEE.

Kamp et al.; Fast Decoder Side Motion Vector Derivation for Inter Frame Video Coding; 2009 Picture Coding Symposium; May 6-8, 2009; IEEE; Chicago, IL, USA.

Chen et al.; From QoS to QoE: A Tutorial on Video Quality Assessment; IEEE Communication Surveys & Tutorials, vol. 17, No. 2, Second Quarter 2015; Oct. 22, 2014; pp. 1126-1165; IEEE.

Bae et al.; HEVC-Based Perceptually Adaptive Video Coding Using a DCT-Based Local Distortion Detection Probability Model; IEEE Transactions on Image Processing, vol. 25, No. 7, Jul. 2016; May 13, 2016; pp. 3343-3357; IEEE.

Sollinger et al.; Non-reference image quality assessment and natural scene statistics to counter biometric sensor spoofing; IET Biometrics; Jan. 2018; pp. 314-324; IET.

Liu et al.; No-Reference Image Quality Assessment Method Based on Visual Parameters; Journal of Electronic Science and Technology, vol. 17, No. 2, Jun. 2019; pp. 171-184.

ZHU; No. reference Video Quality Assessment and Applications; Dissertation submitted for the degree of Doctor of Nature Science; May 8, 2014; Konstanzer Online-Publikations-System (KOPS).

Sogaard et al.; No. Reference Video Quality Assessment using Codec Analysis; IEEE Transactions on Circuits and Systems for Video Technology; Feb. 3, 2015; IEEE.

Xu et al.; No. reference/blind image quality assessment: a survey; IETE Technical Review; Apr. 8, 2016; IETE.

Jiang et al.; On Derivation of Most Probable Modes for Intra Prediction in Video Coding; 2018 IEEE International Symposium on Circuits and Systems (ISCAS); May 27-30, 2018; IEEE; Florence, Italy.

Bianco et al.; On the Use of Deep Learning for Blind Image Quality Assessment; arXiv:1602.05531v5 [cs.CV]; Apr. 4, 2017.

Yang; Perceptual Quality Assessment for Compressed Video; A dissertation submitted in partial satisfaction of the requirements for the degree Doctor of Philosophy in Electrical Engineering (Signal and Image Processing); 2007.

Romaniak et al.; Perceptual quality assessment for H.264/AVC compression; 2012 IEEE Consumer Communications and Networking Conference (CCNC); Jan. 14-17, 2012; IEEE; Las Vegas, NV, USA.

Liu et al.; RankIQA: Learning from Rankings for No-reference Image Quality Assessment; Proceedings of the IEEE International Conference on Computer Vision (ICCV), 2017; Jul. 26, 2017.

Rouis et al.; Study of No-Reference Video Quality Metrics for HEVC Compression; Journal of Telecommunications and Information Technology; 2016; pp. 22-28.

Zhang et al.; Blind Image Quality Assessment Using a Deep Bilinear Convolutional Neural Network; IEEE Transactions on Circuits and Systems for Video Technology, vol. 30, No. 1, Jan. 2020; Dec. 14, 2018; pp. 36-47; IEEE.

Zhang et al.; The Unreasonable Effectiveness of Deep Features as a Perceptual Metric; arXiv:1801.03924v2 [cs.CV]; Apr. 10, 2018.

* cited by examiner

The quick brown fox jumps over the lazy dog. The quick brown fox jumps over the lazy dog. The quick brown fox jumps over the lazy dog.

*FIG. 16*

NO REFERENCE IMAGE QUALITY ASSESSMENT BASED DECODER SIDE INTRA PREDICTION

CROSS-REFERENCE TO RELATED APPLICATIONS

This application claims the benefit of U.S. Provisional Application No. 63/113,230, filed Nov. 13, 2020, which is hereby incorporated by reference in its entirety.

BRIEF DESCRIPTION OF THE DRAWINGS

Examples of several of the various embodiments of the present disclosure are described herein with reference to the drawings.

FIG. 16 illustrates an example of IBC applied for screen content in accordance with embodiments of the present disclosure.

DETAILED DESCRIPTION

Figure 1:
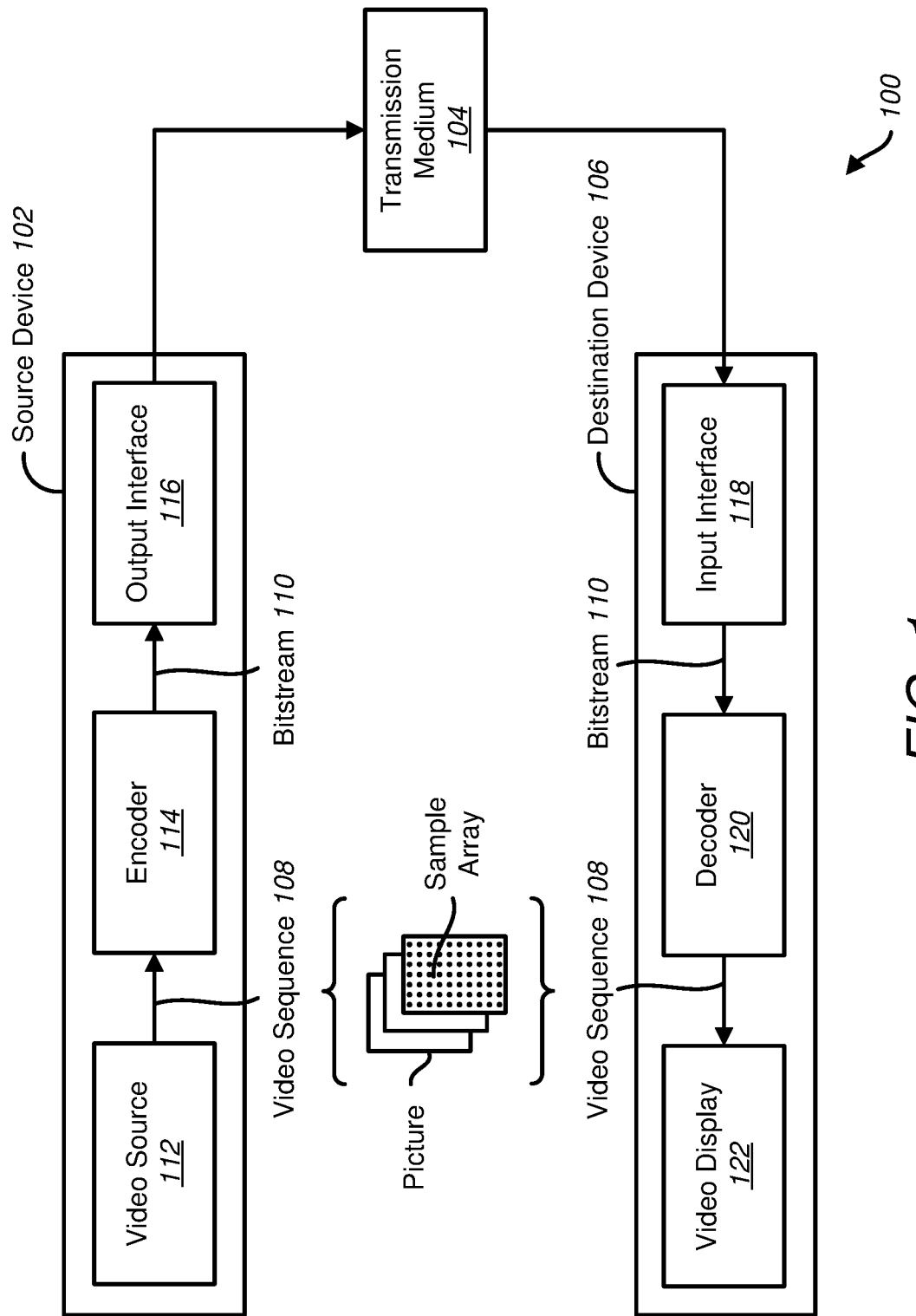
FIG. 1 illustrates an exemplary video coding/decoding system in which embodiments of the present disclosure may be implemented.

In the following description, numerous specific details are set forth in order to provide a thorough understanding of the disclosure. However, it will be apparent to those skilled in the art that the disclosure, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring aspects of the disclosure.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Also, it is noted that individual embodiments may be described as a process which is depicted as a flowchart, a flow diagram, a data flow diagram, a structure diagram, or a block diagram. Although a flowchart may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium. A processor(s) may perform the necessary tasks.

Representing a video sequence in digital form may require a large number of bits. The data size of a video sequence in digital form may be too large for storage and/or transmission in many applications. Video encoding may be used to compress the size of a video sequence to provide for more efficient storage and/or transmission. Video decoding may be used to decompress a compressed video sequence for display and/or other forms of consumption.

FIG. 1 illustrates an exemplary video coding/decoding system 100 in which embodiments of the present disclosure may be implemented. Video coding/decoding system 100 comprises a source device 102, a transmission medium 104, and a destination device 106. Source device 102 encodes a video sequence 108 into a bitstream 110 for more efficient storage and/or transmission. Source device 102 may store and/or transmit bitstream 110 to destination device 106 via transmission medium 104. Destination device 106 decodes bitstream 110 to display video sequence 108. Destination device 106 may receive encoded bit stream 110 from source device 102 via transmission medium 104. Source device 102 and destination device 106 may be any one of a number of different devices, including a desktop computer, laptop computer, tablet computer, smart phone, wearable device, television, camera, video gaming console, set-top box, or video streaming device.

To encode video sequence 108 into bitstream 110, source device 102 may comprise a video source 112, an encoder 114, and an output interface 116. Video source 112 may provide or generate video sequence 108 from a capture of a natural scene and/or a synthetically generated scene. A synthetically generated scene may be a scene comprising computer generated graphics or screen content. Video source 112 may comprise a video capture device (e.g., a video camera), a video archive comprising previously captured natural scenes and/or synthetically generated scenes, a video feed interface to receive captured natural scenes and/or synthetically generated scenes from a video content provider, and/or a processor to generate synthetic scenes.

A shown in FIG. 1, a video sequence, such as video sequence 108, may comprise a series of pictures (also referred to as frames). A video sequence may achieve the impression of motion when a constant or variable time is used to successively present pictures of the video sequence. A picture may comprise one or more sample arrays of intensity values. The intensity values may be taken at a series of regularly spaced locations within a picture. A color picture typically comprises a luminance sample array and two chrominance sample arrays. The luminance sample array may comprise intensity values representing the brightness (or luma component, Y) of a picture. The chrominance sample arrays may comprise intensity values that respectively represent the blue and red components of a picture (or chroma components, Cb and Cr) separate from the brightness. Other color picture sample arrays are possible based on different color schemes (e.g., an RGB color scheme). For color pictures, a pixel may refer to all three intensity values for a given location in the three sample arrays used to represent color pictures. A monochrome picture comprises a single, luminance sample array. For monochrome pictures, a pixel may refer to the intensity value at a given location in the single, luminance sample array used to represent monochrome pictures.

Encoder 114 may encode video sequence 108 into bitstream 110. To encode video sequence 108, encoder 114 may apply one or more prediction techniques to reduce redundant information in video sequence 108. Redundant information is information that may be predicted at a decoder and therefore may not be needed to be transmitted to the decoder for accurate decoding of the video sequence. For example, encoder 114 may apply spatial prediction (e.g., intra-frame or intra prediction), temporal prediction (e.g., inter-frame prediction or inter prediction), inter-layer prediction, and/or other prediction techniques to reduce redundant information in video sequence 108. Before applying the one or more prediction techniques, encoder 114 may partition pictures of video sequence 108 into rectangular regions referred to as blocks. Encoder 114 may then encode a block using one or more of the prediction techniques.

For temporal prediction, encoder 114 may search for a block similar to the block being encoded in another picture (also referred to as a reference picture) of video sequence 108. The block determined during the search (also referred to as a prediction block) may then be used to predict the block being encoded. For spatial prediction, encoder 114 may form a prediction block based on data from reconstructed neighboring samples of the block to be encoded within the same picture of video sequence 108. A reconstructed sample refers to a sample that was encoded and then decoded. Encoder 114 may determine a prediction error (also referred to as a residual) based on the difference between a block being encoded and a prediction block. The prediction error may represent non-redundant information that may be transmitted to a decoder for accurate decoding of a video sequence.

Encoder 114 may apply a transform to the prediction error (e.g. a discrete cosine transform (DCT)) to generate transform coefficients. Encoder 114 may form bitstream 110 based on the transform coefficients and other information used to determine prediction blocks (e.g., prediction types, motion vectors, and prediction modes). In some examples, encoder 114 may perform one or more of quantization and entropy coding of the transform coefficients and/or the other information used to determine prediction blocks before forming bitstream 110 to further reduce the number of bits needed to store and/or transmit video sequence 108.

Output interface 116 may be configured to write and/or store bitstream 110 onto transmission medium 104 for transmission to destination device 106. In addition or alternatively, output interface 116 may be configured to transmit, upload, and/or stream bitstream 110 to destination device 106 via transmission medium 104. Output interface 116 may comprise a wired and/or wireless transmitter configured to transmit, upload, and/or stream bitstream 110 according to one or more proprietary and/or standardized communication protocols, such as Digital Video Broadcasting (DVB) standards, Advanced Television Systems Committee (ATSC) standards, Integrated Services Digital Broadcasting (ISDB) standards, Data Over Cable Service Interface Specification (DOCSIS) standards, 3rd Generation Partnership Project (3GPP) standards, Institute of Electrical and Electronics Engineers (IEEE) standards, Internet Protocol (IP) standards, and Wireless Application Protocol (WAP) standards.

Transmission medium 104 may comprise a wireless, wired, and/or computer readable medium. For example, transmission medium 104 may comprise one or more wires, cables, air interfaces, optical discs, flash memory, and/or magnetic memory. In addition or alternatively, transmission medium 104 may comprise one more networks (e.g., the Internet) or file servers configured to store and/or transmit encoded video data.

To decode bitstream 110 into video sequence 108 for display, destination device 106 may comprise an input interface 118, a decoder 120, and a video display 122. Input interface 118 may be configured to read bitstream 110 stored on transmission medium 104 by source device 102. In addition or alternatively, input interface 118 may be configured to receive, download, and/or stream bitstream 110 from source device 102 via transmission medium 104. Input interface 118 may comprise a wired and/or wireless receiver configured to receive, download, and/or stream bitstream 110 according to one or more proprietary and/or standardized communication protocols, such as those mentioned above.

Decoder 120 may decode video sequence 108 from encoded bit stream 110. To decode video sequence 108, decoder 120 may generate prediction blocks for pictures of video sequence 108 in a similar manner as encoder 114 and determine prediction errors for the blocks. Decoder 120 may generate the prediction blocks using prediction types, prediction modes, and/or motion vectors received in encoded bit stream 110 and determine the prediction errors using transform coefficients also received in encoded bit stream 110. Decoder 120 may determine the prediction errors by weighting transform basis functions using the transform coefficients. Decoder 120 may combine the prediction blocks and prediction errors to decode video sequence 108.

In some examples, decoder 120 may decode a video sequence that approximates video sequence 108 due to, for example, lossy compression of video sequence 108 by encoder 114 and/or errors introduced into encoded bit stream 110 during transmission to destination device 106.

Video display 122 may display video sequence 108 to a user. Video display 122 may comprise a cathode rate tube (CRT) display, liquid crystal display (LCD), a plasma display, light emitting diode (LED) display, or any other display device suitable for displaying video sequence 108.

It should be noted that video encoding/decoding system 100 is presented by way of example and not limitation. In the example of FIG. 1, video encoding/decoding system 100 may have other components and/or arrangements. For example, video source 112 may be external to source device 102. Similarly, video display device 122 may be external to destination device 106 or omitted altogether where video sequence is intended for consumption by a machine and/or storage device. In another example, source device 102 may further comprise a video decoder and destination device 104 may comprise a video encoder. In such an example, source device 102 may be configured to further receive an encoded bit stream from destination device 106 to support two-way video transmission between the devices.

In the example of FIG. 1, encoder 114 and decoder 120 may operate according to any one of a number of proprietary or industry video coding standards. For example, encoder 114 and decoder 120 may operate according to one or more of International Telecommunications Union Telecommunication Standardization Sector (ITU-T) H.263, ITU-T H.264 and Moving Picture Expert Group (MPEG)-4 Visual (also known as Advanced Video Coding (AVC)), ITU-T H.265 and MPEG-H Part 2 (also known as High Efficiency Video Coding (HEVC), ITU-T H.265 and MPEG-I Part 3 (also known as Versatile Video Coding (VVC)), the WebM VP8 and VP9 codecs, and AOMedia Video 1 (AV1).

Figure 2:
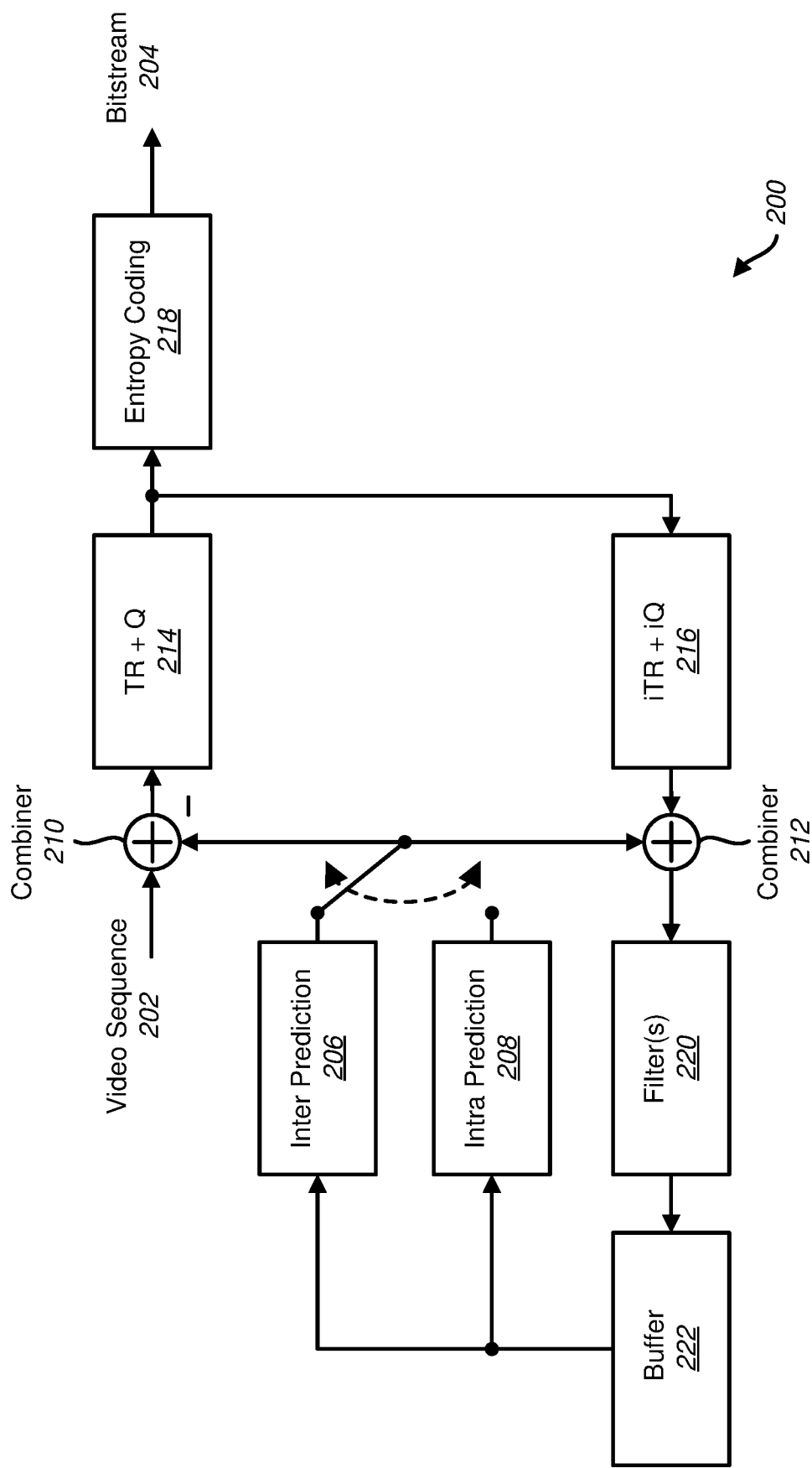
FIG. 2 illustrates an exemplary encoder in which embodiments of the present disclosure may be implemented.

FIG. 2 illustrates an exemplary encoder 200 in which embodiments of the present disclosure may be implemented. Encoder 200 encodes a video sequence 202 into a bitstream 204 for more efficient storage and/or transmission. Encoder 200 may be implemented in video coding/decoding system 100 in FIG. 1 or in any one of a number of different devices, including a desktop computer, laptop computer, tablet computer, smart phone, wearable device, television, camera, video gaming console, set-top box, or video streaming device. Encoder 200 comprises an inter prediction unit 206, an intra prediction unit 208, combiners 210 and 212, a transform and quantization unit (TR+Q) unit 214, an inverse transform and quantization unit (iTR+iQ) 216, entropy coding unit 218, one or more filters 220, and a buffer 222.

Encoder 200 may partition the pictures of video sequence 202 into blocks and encode video sequence 202 on a block-by-block basis. Encoder 200 may perform a prediction technique on a block being encoded using either inter prediction unit 206 or intra prediction unit 208. Inter prediction unit 206 may perform inter prediction by searching for a block similar to the block being encoded in another, reconstructed picture (also referred to as a reference picture) of video sequence 202. A reconstructed picture refers to a picture that was encoded and then decoded. The block determined during the search (also referred to as a prediction block) may then be used to predict the block being encoded to remove redundant information. Inter prediction unit 206 may exploit temporal redundancy or similarities in scene content from picture to picture in video sequence 202 to determine the prediction block. For example, scene content between pictures of video sequence 202 may be similar except for differences due to motion or affine transformation of the screen content over time.

Intra prediction unit 208 may perform intra prediction by forming a prediction block based on data from reconstructed neighboring samples of the block to be encoded within the same picture of video sequence 202. A reconstructed sample refers to a sample that was encoded and then decoded. Intra prediction unit 208 may exploit spatial redundancy or similarities in scene content within a picture of video sequence 202 to determine the prediction block. For example, the texture of a region of scene content in a picture may be similar to the texture in the immediate surrounding area of the region of the scene content in the same picture.

After prediction, combiner 210 may determine a prediction error (also referred to as a residual) based on the difference between the block being encoded and the prediction block. The prediction error may represent non-redundant information that may be transmitted to a decoder for accurate decoding of a video sequence.

Transform and quantization unit 214 may transform and quantize the prediction error. Transform and quantization unit 214 may transform the prediction error into transform coefficients by applying, for example, a DCT to reduce correlated information in the prediction error. Transform and quantization unit 214 may quantize the coefficients by mapping data of the transform coefficients to a predefined set of representative values. Transform and quantization unit 214 may quantize the coefficients to reduce irrelevant information in bitstream 204. Irrelevant information is information that may be removed from the coefficients without producing visible and/or perceptible distortion in video sequence 202 after decoding.

Entropy coding unit 218 may apply one or more entropy coding methods to the quantized transform coefficients to further reduce the bit rate. For example, entropy coding unit 218 may apply context adaptive variable length coding (CAVLC), context adaptive binary arithmetic coding (CABAC), and syntax-based context-based binary arithmetic coding (SBAC). The entropy coded coefficients are packed to form bitstream 204.

Inverse transform and quantization unit 216 may inverse quantize and inverse transform the quantized transform coefficients to determine a reconstructed prediction error. Combiner 212 may combine the reconstructed prediction error with the prediction block to form a reconstructed block. Filter(s) 220 may filter the reconstructed block using, for example, a deblocking filter and/or a sample-adaptive offset (SAO) filter. Buffer 222 may store the reconstructed block for prediction of one or more other blocks in the same and/or different picture of video sequence 202.

Although not shown in FIG. 2, encoder 200 further comprises an encoder control unit configured to control one or more of the units of encoder 200 shown in FIG. 2. The encoder control unit may control the one or more units of encoder 200 such that bitstream 204 is generated in conformance with the requirements of any one of a number of proprietary or industry video coding standards. For example, The encoder control unit may control the one or more units of encoder 200 such that bitstream 204 is generated in conformance with one or more of ITU-T H.263, AVC, HEVC, VVC, VP8, VP9, and AV1 video coding standards.

Within the constraints of a proprietary or industry video coding standard, the encoder control unit may attempt to minimize or reduce the bitrate of bitstream 204 and maximize or increase the reconstructed video quality. For example, the encoder control unit may attempt to minimize or reduce the bitrate of bitstream 204 given a level that the reconstructed video quality may not fall below, or attempt to maximize or increase the reconstructed video quality given a level that the bit rate of bitstream 204 may not exceed. The encoder control unit may determine/control one or more of: partitioning of the pictures of video sequence 202 into blocks, whether a block is inter predicted by inter prediction unit 206 or intra predicted by intra prediction unit 208, a motion vector for inter prediction of a block, an intra prediction mode among a plurality of intra prediction modes for intra prediction of a block, filtering performed by filter(s) 220, and one or more transform types and/or quantization parameters applied by transform and quantization unit 214. The encoder control unit may determine/control the above based on how the determination/control effects a rate-distortion measure for a block or picture being encoded. The encoder control unit may determine/control the above to reduce the rate-distortion measure for a block or picture being encoded.

After being determined, the prediction type used to encode a block (intra or inter prediction), prediction information of the block (intra prediction mode if intra predicted, motion vector, etc.), and transform and quantization parameters, may be sent to entropy coding unit 218 to be further compressed to reduce the bit rate. The prediction type, prediction information, and transform and quantization parameters may be packed with the prediction error to form bitstream 204.

It should be noted that encoder 200 is presented by way of example and not limitation. In other examples, encoder 200 may have other components and/or arrangements. For example, one or more of the components shown in FIG. 2 may be optionally included in encoder 200, such as entropy coding unit 218 and filters(s) 220.

Figure 3:
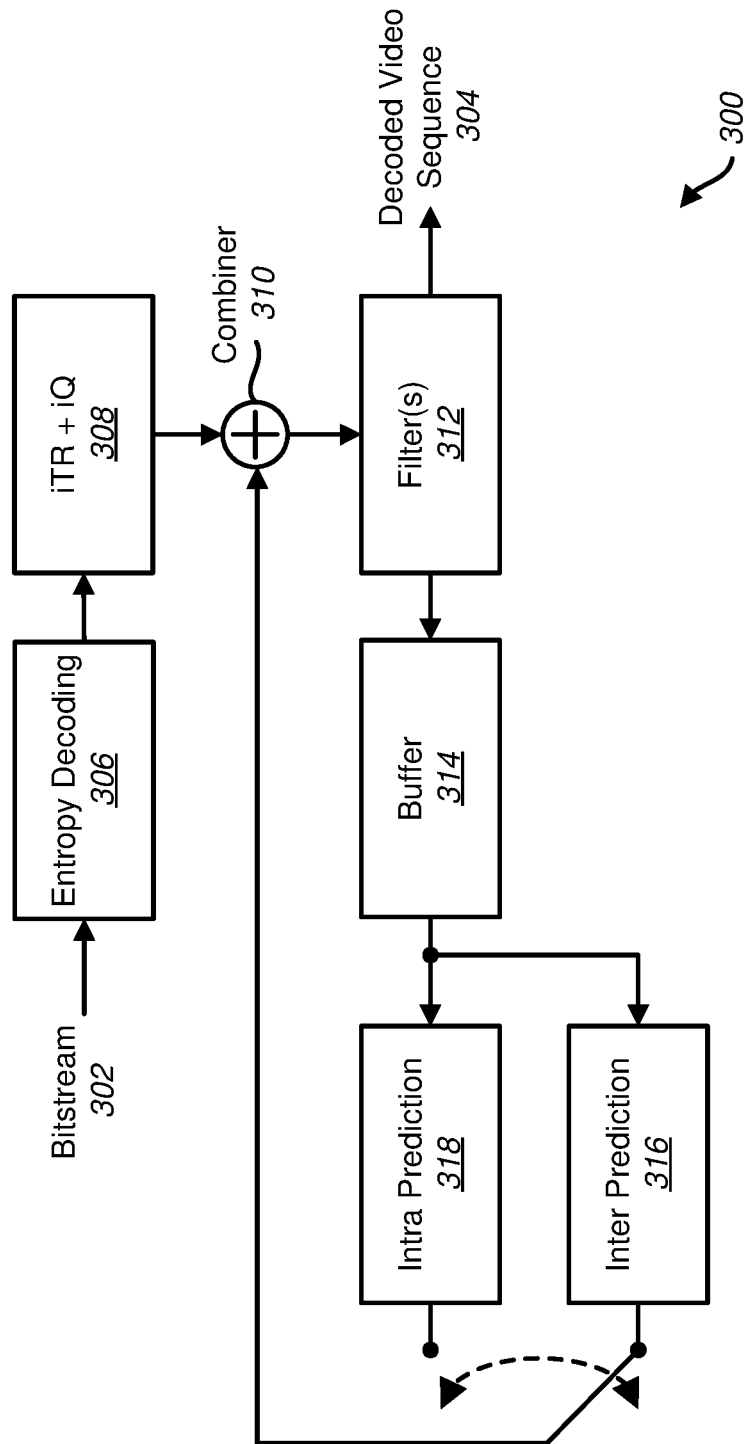
FIG. 3 illustrates an exemplary decoder in which embodiments of the present disclosure may be implemented.

FIG. 3 illustrates an exemplary decoder 300 in which embodiments of the present disclosure may be implemented. Decoder 300 decodes a bitstream 302 into a decoded video sequence for display and/or some other form of consumption. Decoder 300 may be implemented in video coding/decoding system 100 in FIG. 1 or in any one of a number of different devices, including a desktop computer, laptop computer, tablet computer, smart phone, wearable device, television, camera, video gaming console, set-top box, or video streaming device. Decoder 300 comprises an entropy decoding unit 306, an inverse transform and quantization (iTR+iQ) unit 308, a combiner 310, one or more filters 312, a buffer 314, an inter prediction unit 316, and an intra prediction unit 318.

Although not shown in FIG. 3, decoder 300 further comprises a decoder control unit configured to control one or more of the units of decoder 300 shown in FIG. 3. The decoder control unit may control the one or more units of decoder 300 such that bitstream 302 is decoded in conformance with the requirements of any one of a number of proprietary or industry video coding standards. For example, The decoder control unit may control the one or more units of decoder 300 such that bitstream 302 is decoded in conformance with one or more of ITU-T H.263, AVC, HEVC, VVC, VP8, VP9, and AV1 video coding standards.

The decoder control unit may determine/control one or more of: whether a block is inter predicted by inter prediction unit 316 or intra predicted by intra prediction unit 318, a motion vector for inter prediction of a block, an intra prediction mode among a plurality of intra prediction modes for intra prediction of a block, filtering performed by filter(s) 312, and one or more inverse transform types and/or inverse quantization parameters to be applied by inverse transform and quantization unit 308. One or more of the control parameters used by the decoder control unit may be packed in bitstream 302.

Entropy decoding unit 306 may entropy decode the bitstream 302. Inverse transform and quantization unit 308 may inverse quantize and inverse transform the quantized transform coefficients to determine a decoded prediction error. Combiner 310 may combine the decoded prediction error with a prediction block to form a decoded block. The prediction block may be generated by inter prediction unit 318 or inter prediction unit 316 as described above with respect to encoder 200 in FIG. 2. Filter(s) 312 may filter the decoded block using, for example, a deblocking filter and/or a sample-adaptive offset (SAO) filter. Buffer 314 may store the decoded block for prediction of one or more other blocks in the same and/or different picture of the video sequence in bitstream 302. Decoded video sequence 304 may be output from filter(s) 312 as shown in FIG. 3.

It should be noted that decoder 300 is presented by way of example and not limitation. In other examples, decoder 300 may have other components and/or arrangements. For example, one or more of the components shown in FIG. 3 may be optionally included in decoder 300, such as entropy decoding unit 306 and filters(s) 312.

It should be further noted that, although not shown in FIGS. 2 and 3, each of encoder 200 and decoder 300 may further comprise an intra block copy unit in addition to inter prediction and intra prediction units. The intra block copy unit may perform similar to an inter prediction unit but predict blocks within the same picture. For example, the intra block copy unit may exploit repeated patterns that appear in screen content. Screen content may include, for example, computer generated text, graphics, and animation.

As mentioned above, video encoding and decoding may be performed on a block-by-block basis. The process of partitioning a picture into blocks may be adaptive based on the content of the picture. For example, larger block partitions may be used in areas of a picture with higher levels of homogeneity to improve coding efficiency.

In HEVC, a picture may be partitioned into non-overlapping square blocks, referred to as coding tree blocks (CTBs), comprising samples of a sample array. A CTB may have a size of $2^n \times 2^n$ samples, where n may be specified by a parameter of the encoding system. For example, n may be 4, 5, or 6. A CTB may be further partitioned by a recursive quadtree partitioning into coding blocks (CBs) of half vertical and half horizontal size. The CTB forms the root of the quadtree. A CB that is not split further as part of the recursive quadtree partitioning may be referred to as a leaf-CB of the quadtree and otherwise as a non-leaf CB of the quadtree. A CB may have a minimum size specified by a parameter of the encoding system. For example, a CB may have a minimum size of 4×4, 8×8, 16×16, 32×32, or 64×64 samples. For inter and intra prediction, a CB may be further partitioned into one or more prediction blocks (PBs) for performing inter and intra prediction. A PB may be a rectangular block of samples on which the same prediction type/mode may be applied. For transformations, a CB may be partitioned into one or more transform blocks (TBs). A TB may be a rectangular block of samples that may determine an applied transform size.

Figure 4:
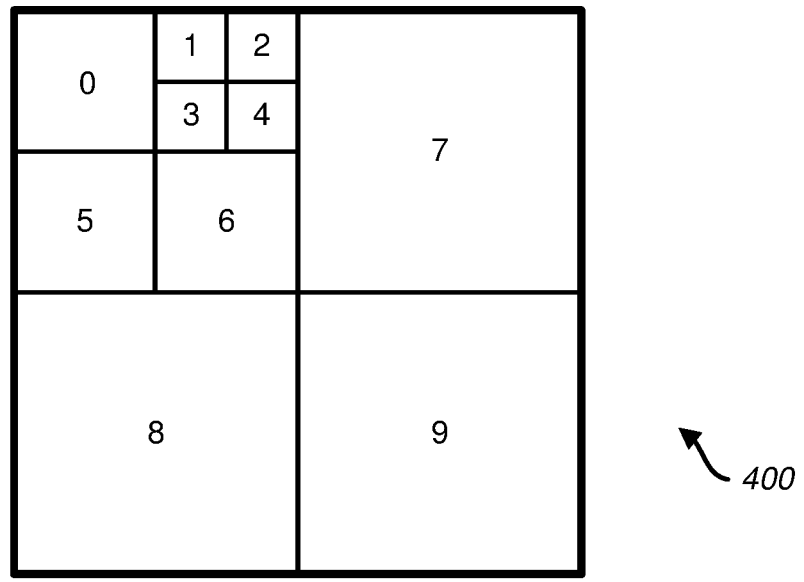
FIG. 4 illustrates an example quadtree partitioning of a coding tree block (CTB) in accordance with embodiments of the present disclosure.
Figure 5:
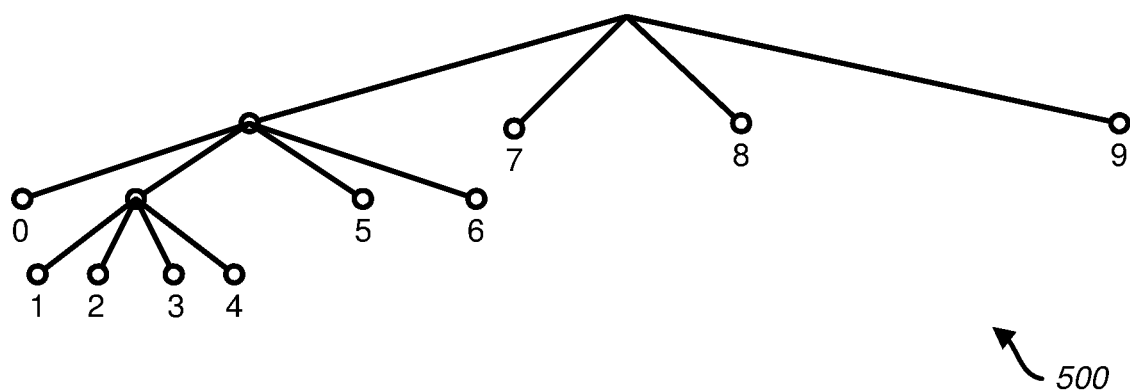
FIG. 5 illustrates a corresponding quadtree of the example quadtree partitioning of the CTB in FIG. 4 in accordance with embodiments of the present disclosure.

FIG. 4 illustrates an example quadtree partitioning of a CTB 400. FIG. 5 illustrates a corresponding quadtree 500 of the example quadtree partitioning of CTB 400 in FIG. 4. As shown in FIGS. 4 and 5, CTB 400 is first partitioned into four CBs of half vertical and half horizontal size. Three of the resulting CBs of the first level partitioning of CTB 400 are leaf-CBs. The three leaf CBs of the first level partitioning of CTB 400 are respectively labeled 7, 8, and 9 in FIGS. 4 and 5. The non-leaf CB of the first level partitioning of CTB 400 is partitioned into four sub-CBs of half vertical and half horizontal size. Three of the resulting sub-CBs of the second level partitioning of CTB 400 are leaf CBs. The three leaf CBs of the second level partitioning of CTB 400 are respectively labeled 0, 5, and 6 in FIGS. 4 and 5. Finally, the non-leaf CB of the second level partitioning of CTB 400 is partitioned into four leaf CBs of half vertical and half horizontal size. The four leaf CBs are respectively labeled 1, 2, 3, and 4 in FIGS. 4 and 5.

Altogether, CTB 400 is partitioned into 10 leaf CBs respectively labeled 0-9. The resulting quadtree partitioning of CTB 400 may be scanned using a z-scan (left-to-right, top-to-bottom) to form the sequence order for encoding/decoding the CB leaf nodes. The numeric label of each CB leaf node in FIGS. 4 and 5 may correspond to the sequence order for encoding/decoding, with CB leaf node 0 encoded/decoded first and CB leaf node 9 encoded/decoded last. Although not shown in FIGS. 4 and 5, it should be noted that each CB leaf node may comprise one or more PBs and TBs.

Figure 6:
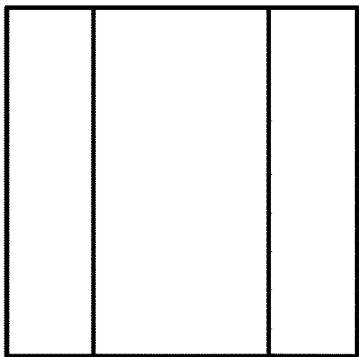
FIG. 6 illustrates example binary and ternary tree partitions in accordance with embodiments of the present disclosure.
Figure 6:
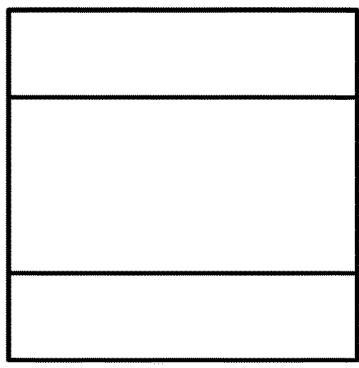
Figure 6:
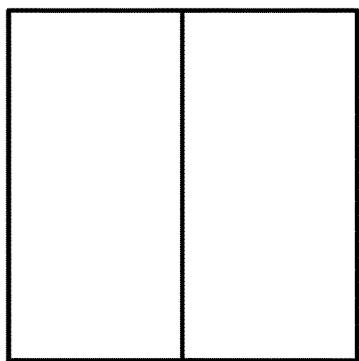
Figure 6:
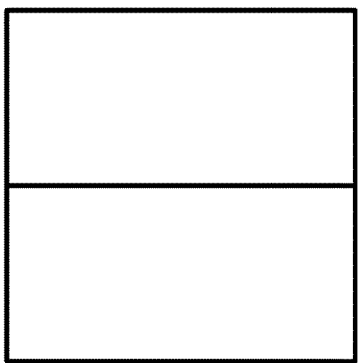

In VVC, a picture may be partitioned in a similar manner as in HEVC. A picture may be first partitioned into non-overlapping square CTBs. The CTBs may then be partitioned by a recursive quadtree partitioning into CBs of half vertical and half horizontal size. In VVC, a quadtree leaf node may be further partitioned by a binary tree or ternary tree partitioning into CBs of unequal sizes. FIG. 6 illustrates example binary and ternary tree partitions. A binary tree partition may divide a parent block in half in either the vertical direction 602 or horizontal direction 604. The resulting partitions may be half in size as compared to the parent block. A ternary tree partition may divide a parent block into three parts in either the vertical direction 606 or horizontal direction 608. The middle partition may be twice as large as the other two end partitions in a ternary tree partition.

Figure 7:
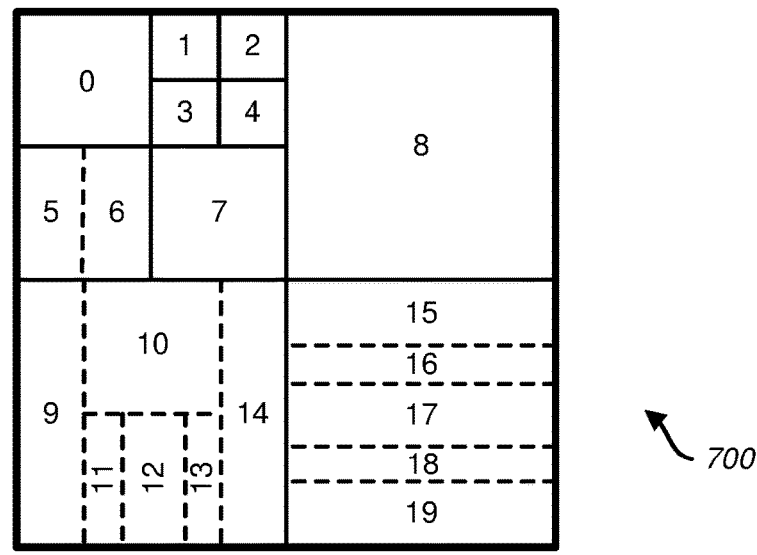
FIG. 7 illustrates an example quadtree+multi-type tree partitioning of a CTB in accordance with embodiments of the present disclosure.
Figure 8:
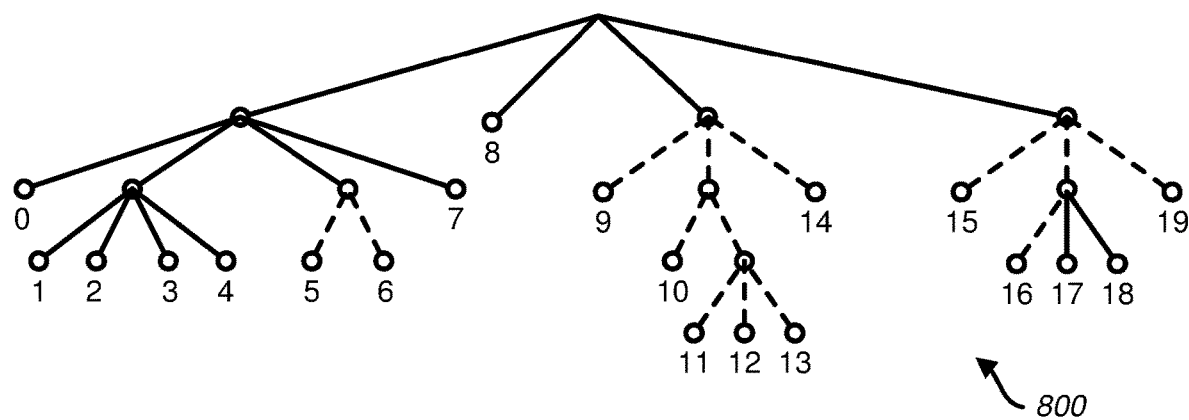
FIG. 8 illustrates a corresponding quadtree+multi-type tree of the example quadtree+multi-type tree partitioning of the CTB in FIG. 7 in accordance with embodiments of the present disclosure.

Because of the addition of binary and ternary tree partitioning, in VVC the block partitioning strategy may be referred to as quadtree+multi-type tree partitioning. FIG. 7 illustrates an example quadtree+multi-type tree partitioning of a CTB 700. FIG. 8 illustrates a corresponding quadtree+multi-type tree 800 of the example quadtree+multi-type tree partitioning of CTB 700 in FIG. 7. In both FIGS. 7 and 8, quadtree splits are shown in solid lines and multi-type tree splits are shown in dashed lines. For ease of explanation, CTB 700 is shown with the same quadtree partitioning as CTB 400 described in FIG. 4. Therefore, description of the quadtree partitioning of CTB 700 is omitted. The description of the additional multi-type tree partitions of CTB 700 is made relative to three leaf-CBs shown in FIG. 4 that have been further partitioned using one or more binary and ternary tree partitions. The three leaf-CBs in FIG. 4 that are shown in FIG. 7 as being further partitioned are leaf-CBs 5, 8, and 9.

Starting with leaf-CB 5 in FIG. 4, FIG. 7 shows this leaf-CB partitioned into two CBs based on a vertical binary tree partitioning. The two resulting CBs are leaf-CBs respectively labeled 5 and 6 in FIGS. 7 and 8. With respect to leaf-CB 8 in FIG. 4, FIG. 7 shows this leaf-CB partitioned into three CBs based on a vertical ternary tree partition. Two of the three resulting CBs are leaf-CBs respectively labeled 9 and 14 in FIGS. 7 and 8. The remaining, non-leaf CB is partitioned first into two CBs based on a horizontal binary tree partition, one of which is a leaf-CB labeled 10 and the other of which is further partitioned into three CBs based on a vertical ternary tree partition. The resulting three CBs are leaf-CBs respectively labeled 11, 12, and 13 in FIGS. 7 and 8. Finally, with respect to leaf-CB 9 in FIG. 4, FIG. 7 shows this leaf-CB partitioned into three CBs based on a horizontal ternary tree partition. Two of the three CBs are leaf-CBs respectively labeled 15 and 19 in FIGS. 7 and 8. The remaining, non-leaf CB is partitioned into three CBs based on another horizontal ternary tree partition. The resulting three CBs are all leaf-CBs respectively labeled 16, 17, and 18 in FIGS. 7 and 8.

Altogether, CTB 700 is partitioned into 20 leaf CBs respectively labeled 0-19. The resulting quadtree+multi-type tree partitioning of CTB 700 may be scanned using a z-scan (left-to-right, top-to-bottom) to form the sequence order for encoding/decoding the CB leaf nodes. The numeric label of each CB leaf node in FIGS. 7 and 8 may correspond to the sequence order for encoding/decoding, with CB leaf node 0 encoded/decoded first and CB leaf node 19 encoded/decoded last. Although not shown in FIGS. 7 and 8, it should be noted that each CB leaf node may comprise one or more PBs and TBs.

In addition to specifying various blocks (e.g., CTB, CB, PB, TB), HEVC and VVC further define various units. While blocks may comprise a rectangular area of samples in a sample array, units may comprise the collocated blocks of samples from the different sample arrays (e.g., luma and chroma sample arrays) that form a picture as well as syntax elements and prediction data of the blocks. A coding tree unit (CTU) may comprise the collocated CTBs of the different sample arrays and may form a complete entity in an encoded bit stream. A coding unit (CU) may comprise the collocated CBs of the different sample arrays and syntax structures used to code the samples of the CBs. A prediction unit (PU) may comprise the collocated PBs of the different sample arrays and syntax elements used to predict the PBs. A transform unit (TU) may comprise TBs of the different samples arrays and syntax elements used to transform the TBs.

It should be noted that the term block may be used to refer to any of a CTB, CB, PB, TB, CTU, CU, PU, or TU in the context of HEVC and VVC. It should be further noted that the term block may be used to refer to similar data structures in the context of other video coding standards. For example, the term block may refer to a macroblock in AVC, a macroblock or sub-block in VP8, a superblock or sub-block in VP9, or a superblock or sub-block in AV1.

In intra prediction, samples of a block to be encoded (also referred to as the current block) may be predicted from samples of the column immediately adjacent to the left-most column of the current block and samples of the row immediately adjacent to the top-most row of the current block. The samples from the immediately adjacent column and row may be jointly referred to as reference samples. Each sample of the current block may be predicted by projecting the position of the sample in the current block in a given direction (also referred to as an intra prediction mode) to a point along the reference samples. The sample may be predicted by interpolating between the two closest reference samples of the projection point if the projection does not fall directly on a reference sample. A prediction error (also referred to as a residual) may be determined for the current block based on differences between the predicted sample values and the original sample values of the current block.

At an encoder, this process of predicting samples and determining a prediction error based on a difference between the predicted samples and original samples may be performed for a plurality of different intra prediction modes, including non-directional intra prediction modes. The encoder may select one of the plurality of intra prediction modes and its corresponding prediction error to encode the current block. The encoder may send an indication of the selected prediction mode and its corresponding prediction error to a decoder for decoding of the current block. The decoder may decode the current block by predicting the samples of the current block using the intra prediction mode indicated by the encoder and combining the predicted samples with the prediction error.

Figure 9:
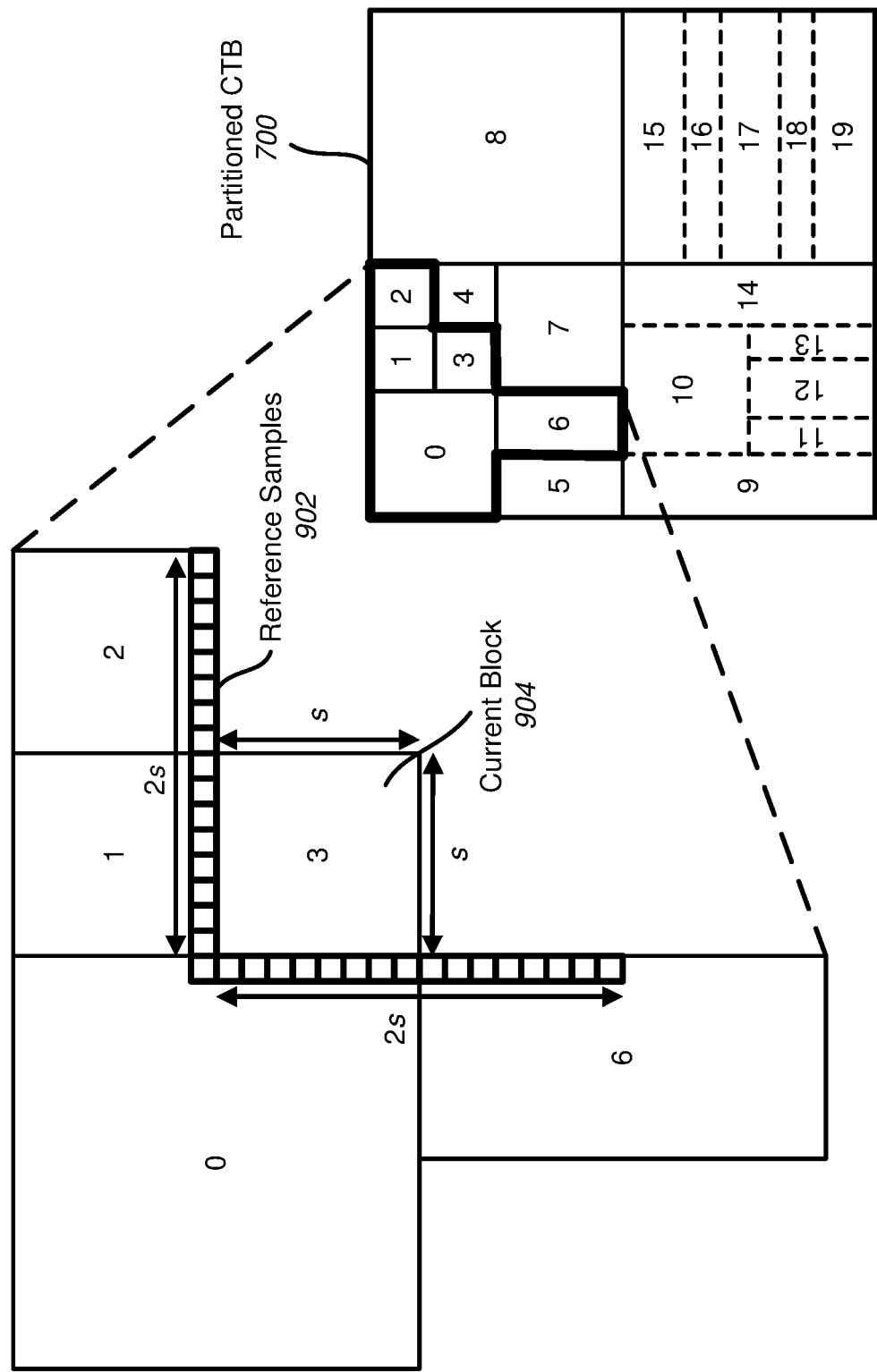
FIG. 9 illustrates an example set of reference samples determined for intra prediction of a current block being encoded or decoded in accordance with embodiments of the present disclosure.

FIG. 9 illustrates an example set of reference samples 902 determined for intra prediction of a current block 904 being encoded or decoded. In FIG. 9, current block 904 corresponds to block 3 of partitioned CTB 700 in FIG. 7. As explained above, the numeric labels 0-19 of the blocks of partitioned CTB 700 may correspond to the sequence order for encoding/decoding the blocks and are used as such in the example of FIG. 9.

Given current block 904 is of w×h samples in size, reference samples 902 may extend over 2w samples of the row immediately adjacent to the top-most row of current block 904, 2h samples of the column immediately adjacent to the left-most column of current block 904, and the top left neighboring corner sample to current block 904. In the example of FIG. 9, current block 904 is square, so w=h=s. For constructing the set of reference samples 902, available samples from neighboring blocks of current block 904 may be used. Samples may not be available for constructing the set of reference samples 902 if, for example, the samples would lie outside the picture of the current block, the samples are part of a different slice of the current block (where the concept of slices are used), and/or the samples belong to blocks that have been inter coded and constrained intra prediction is indicated. When constrained intra prediction is indicated, intra prediction may not be dependent on inter predicted blocks.

In addition to the above, samples that may not be available for constructing the set of reference samples 902 include samples in blocks that have not already been encoded and reconstructed at an encoder or decoded at a decoder based on the sequence order for encoding/decoding. This restriction may allow identical prediction results to be determined at both the encoder and decoder. In FIG. 9, samples from neighboring blocks 0, 1, and 2 may be available to construct reference samples 902 given that these blocks are encoded and reconstructed at an encoder and decoded at a decoder prior to coding of current block 904. This assumes there are no other issues, such as those mentioned above, preventing the availability of samples from neighboring blocks 0, 1, and 2. However, the portion of reference samples 902 from neighboring block 6 may not be available due to the sequence order for encoding/decoding.

Unavailable ones of reference samples 902 may be filled with available ones of reference samples 902. For example, an unavailable reference sample may be filled with a nearest available reference sample determined by moving in a clock-wise direction through reference samples 902 from the position of the unavailable reference. If no reference samples are available, reference samples 902 may be filled with the mid-value of the dynamic range of the picture being coded.

It should be noted that reference samples 902 may be filtered based on the size of current block 904 being coded and an applied intra prediction mode. It should be further noted that FIG. 9 illustrates only one exemplary determination of reference samples for intra prediction of a block. In some proprietary and industry video coding standards, reference samples may be determined in a different manner than discussed above. For example, multiple reference lines may be used in other instances, such as used in VVC.

After reference samples 902 are determined and optionally filtered, samples of current block 904 may be intra predicted based on reference samples 902. Most encoders/decoders support a plurality of intra prediction modes in accordance with one or more video coding standards. For example, HEVC supports 35 intra prediction modes, including a planar mode, a DC mode, and 33 angular modes. VVC supports 67 intra prediction modes, including a planar mode, a DC mode, and 65 angular modes. Planar and DC modes may be used to predict smooth and gradually changing regions of a picture. Angular modes may be used to predict directional structures in regions of a picture.

Figure 10A:
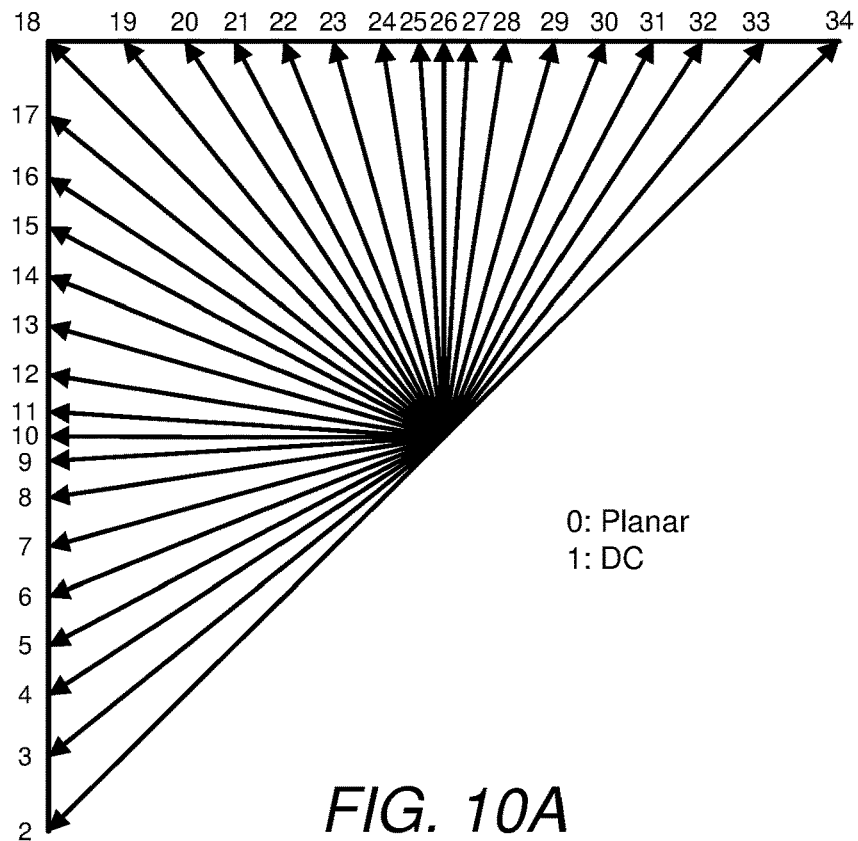
FIG. 10A illustrates the 35 intra prediction modes supported by HEVC in accordance with embodiments of the present disclosure.

FIG. 10A illustrates the 35 intra prediction modes supported by HEVC. The 35 intra prediction modes are identified by indices 0 to 34. Prediction mode 0 corresponds to planar mode. Prediction mode 1 corresponds to DC mode. Prediction modes 2-34 correspond to angular modes. Prediction modes 2-18 may be referred to as horizontal prediction modes because the principal source of prediction is in the horizontal direction. Prediction modes 19-34 may be referred to as vertical prediction modes because the principal source of prediction is in the vertical direction.

Figure 10B:
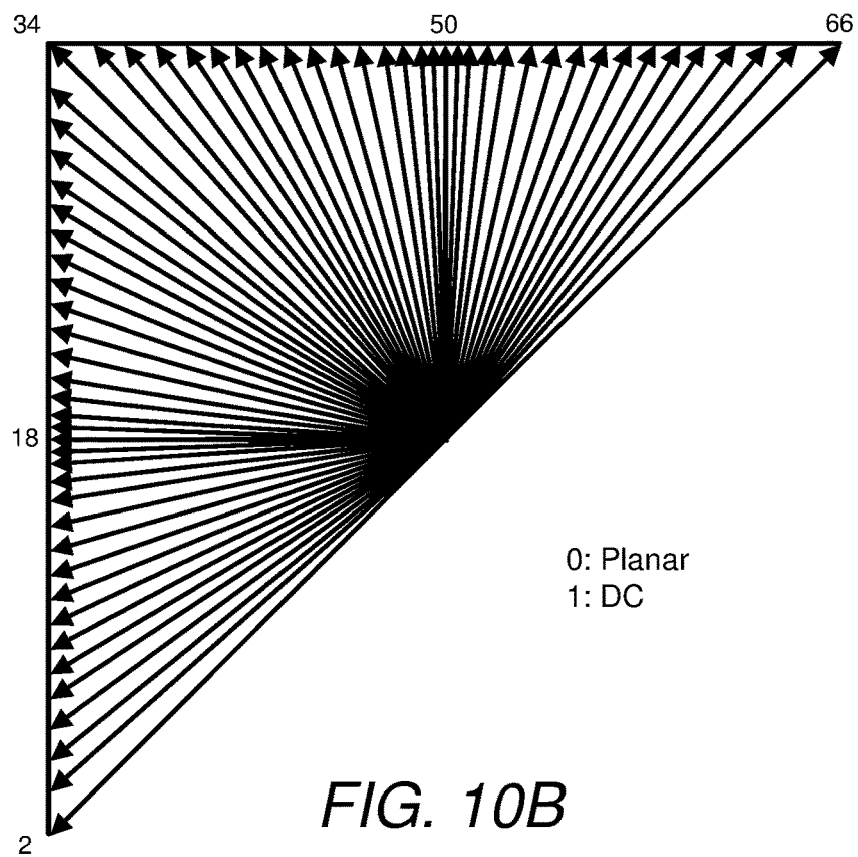
FIG. 10B illustrates the 67 intra prediction modes supported by HEVC in accordance with embodiments of the present disclosure.

FIG. 10B illustrates the 67 intra prediction modes supported by VVC. The 67 intra prediction modes are identified by indices 0 to 66. Prediction mode 0 corresponds to planar mode. Prediction mode 1 corresponds to DC mode. Prediction modes 2-66 correspond to angular modes. Prediction modes 2-34 may be referred to as horizontal prediction modes because the principal source of prediction is in the horizontal direction. Prediction modes 35-66 may be referred to as vertical prediction modes because the principal source of prediction is in the vertical direction. Because blocks in VVC may be non-square, some of the intra prediction modes illustrated in FIG. 10B may be adaptively replaced by wide-angle directions.

Figure 11:
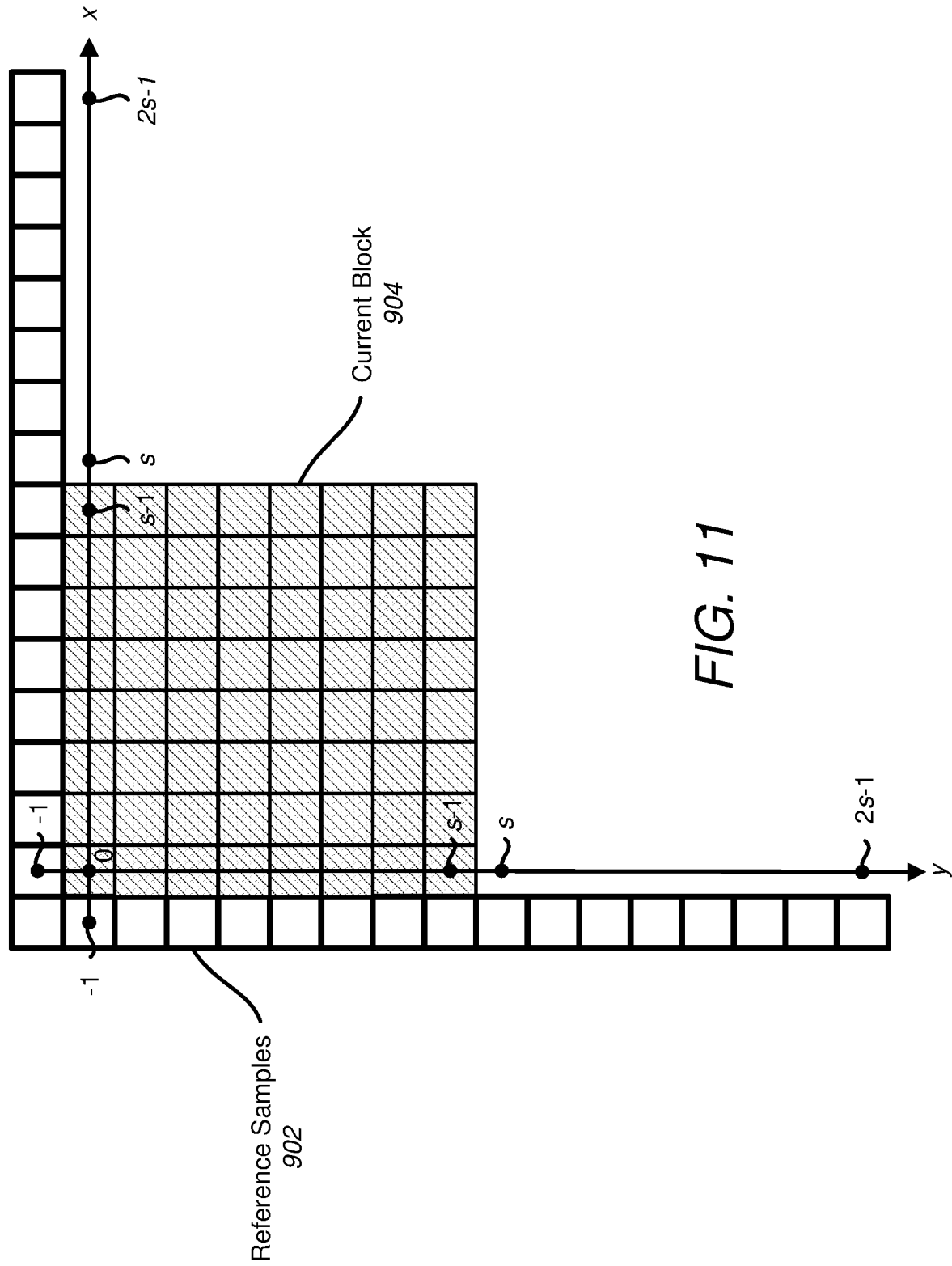
FIG. 11 illustrates the current block and reference samples from FIG. 9 in a two-dimensional x, y plane in accordance with embodiments of the present disclosure.
Figure 12:
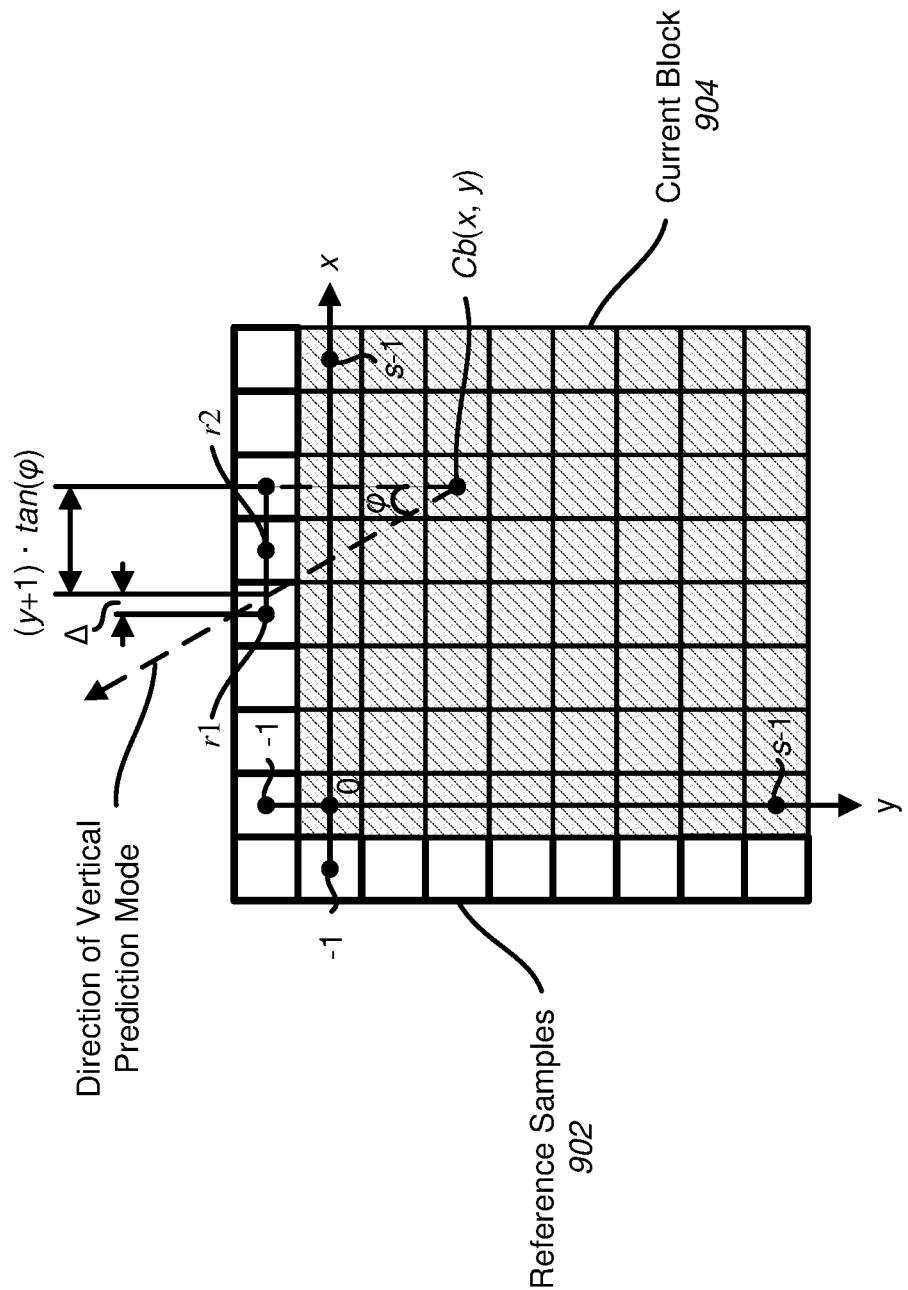
FIG. 12 illustrates an example angular mode prediction of the current block from FIG. 9 in accordance with embodiments of the present disclosure.

To further describe the application of intra prediction modes to determine a prediction of a current block, reference is made to FIGS. 11 and 12. In FIG. 11, current block 904 and reference samples 902 from FIG. 9 are shown in a two-dimensional x, y plane. Current block 904 is referred to as Cb, where Cb(x, y) denotes the predicted value of current block 904 at the coordinates (x, y). Reference samples 902 are referred to as r, where r(x, y) denotes the reference sample of reference samples 902 at the coordinates (x, y).

For planar mode, a sample in Cb may be predicted by calculating the mean of two interpolated values. The first of the two interpolated values may be based on a horizontal linear interpolation of the predicted sample in Cb. The second of the two interpolated values may be based on a vertical linear interpolation of the predicted sample in Cb. The predicted value of the sample in Cb may be calculated as $$Cb(x, y) = \frac{1}{2 \cdot s}(h(x, y) + v(x, y) + s) \quad (1)$$

where $$h(x, y) = (s - x - 1) \cdot r(-1, y) + (x + 1) \cdot r(s, -1) \quad (2)$$

may be the horizontal linear interpolation of the predicted sample in Cb and $$v(x,y) = (s-y-1) \cdot r(x,-1) + (y+1) \cdot r(-1,s) \quad (3)$$

may be the vertical linear interpolation of the predicted sample in Cb.

For DC mode, a sample in Cb may be predicted by the mean of the reference samples. The predicted value of the sample in Cb may be calculated as $$Cb(x, y) = \frac{1}{2 \cdot s} \cdot \left( \sum_{x=0}^{s-1} r(x, -1) + \sum_{y=0}^{s-1} r(-1, y) \right) \quad (4)$$

A boundary filter may be applied to boundary samples in Cb to smooth the transition between the boundary samples and their respective adjacent neighboring reference sample(s) in r.

For angular modes, a sample in Cb may be predicted by projecting the position of the sample in a direction specified by a given angular mode to a point on the horizontal or vertical axis comprising the reference samples r. The sample may be predicted by interpolating between the two closest reference samples in r of the projection point if the projection does not fall directly on a reference sample in r. The direction specified by the angular mode may be given by an angle $\varphi$ defined relative to the y-axis for vertical prediction modes (e.g., modes 19-34 in HEVC and modes 35-66 in VVC) and relative to the x-axis for horizontal prediction modes (e.g., modes 2-18 in HEVC and modes 2-34 in VVC).

FIG. 12 illustrates a sample in Cb predicted for a vertical prediction mode. For vertical prediction modes, the position (x, y) of the sample in Cb is projected onto the horizontal axis comprising reference samples r. Because the projection falls between two reference samples r1 and r2 in the example of FIG. 12, the predicted value of the sample in Cb may be calculated as the linear interpolation between the two reference samples r1 and r2 as $$Cb(x,y) = (1-\Delta)r1 + \Delta \cdot r2 \quad (5)$$

where $$r1 = r(x + \lfloor (y+1) \cdot \tan \varphi \rfloor, -1), \quad (6)$$

$$r2 = r(x + \lfloor (y+1) \cdot \tan \varphi \rfloor + 1, -1), \quad (7)$$

$$\Delta = ((y+1) \cdot \tan \varphi) - \lfloor (y+1) \cdot \tan \varphi \rfloor, \text{ and} \quad (8)$$

$$\lfloor \cdot \rfloor \text{ is an integer floor.} \quad (9)$$

It should be noted that the weighting factors $(1-\Delta)$ and $\Delta$ may be calculated with some predefined level of precision, such as 1/32 pixel precision. To avoid floating point operations while preserving the specified precision, the weighting factors $(1-\Delta)$ and $\Delta$ may be multiplied by the reciprocal of the specified precision used and then divided by the reciprocal using, for example, right shift operations. It should be further noted that supplementary reference samples may be constructed for the case where the position (x, y) of a sample Cb to predicted is projected to a negative x coordinate, which happens with negative angles $\varphi$. The supplementary reference samples may be constructed by projecting the reference samples in r on the vertical axis to the horizontal axis using the angle $\varphi$. Finally, it should be further noted that a sample in Cb may be predicted for a horizontal prediction mode in a similar manner as discussed above for vertical prediction modes. For horizontal prediction modes, the position (x, y) of the sample in Cb may be projected onto the vertical axis comprising reference samples r and the angle $\varphi$ may be defined relative to the x-axis. Supplemental reference samples may be similarly constructed for horizontal prediction modes by projecting the reference samples in r on the horizontal axis to the vertical axis using the angle φ.

An encoder may predict the samples of a current block being encoded, such as current block 904, for a plurality of intra prediction modes as explained above. For example, the encoder may predict the samples of the current block for each of the 35 intra prediction modes in HEVC or 67 intra prediction modes in VVC. For each intra prediction mode applied, the encoder may determine a prediction error for the current block based on a difference (e.g., sum of squared differences (SSD), sum of absolute differences (SAD), or sum of absolute transformed differences (SATD)) between the prediction samples determined for the intra prediction mode and the original samples of the current block. The encoder may select one of the intra prediction modes to encode the current block based on the determined prediction errors. For example, the encoder may select an intra prediction mode that results in the smallest prediction error for the current block. In another example, the encoder may select the intra prediction mode to encode the current block based on a rate-distortion measure (e.g., Lagrangian rate-distortion cost) determined using the prediction errors. The encoder may send an indication of the selected intra prediction mode and its corresponding prediction error to a decoder for decoding of the current block.

Although the description above was primarily made with respect to intra prediction modes in HEVC and VVC, it will be understood that the techniques of the present disclosure described above and further below may be applied to other intra prediction modes, including those of other video coding standards like VP8, VP9, AV1, and the like.

As explained above, intra prediction may exploit correlations between spatially neighboring samples in the same picture of a video sequence to perform video compression. Inter prediction is another coding tool that may be used to exploit correlations in the time domain between blocks of samples in different pictures of the video sequence to perform video compression. In general, an object may be seen across multiple pictures of a video sequence. The object may move (e.g., by some translation and/or affine motion) or remain stationary across the multiple pictures. A current block of samples in a current picture being encoded may therefore have a corresponding block of samples in a previously decoded picture that accurately predicts the current block of samples. The corresponding block of samples may be displaced from the current block of samples due to movement of an object, represented in both blocks, across the respective pictures of the blocks. The previously decoded picture may be referred to as a reference picture and the corresponding block of samples in the reference picture may be referred to as a reference block or motion compensated prediction. An encoder may use a block matching technique to estimate the displacement (or motion) and determine the reference block in the reference picture.

Similar to intra prediction, once a prediction for a current block is determined and/or generated using inter prediction, an encoder may determine a difference between the current block and the prediction. The difference may be referred to as a prediction error or residual. The encoder may then store and/or signal in a bitstream the prediction error and other related prediction information for decoding or other forms of consumption. A decoder may decode the current block by predicting the samples of the current block using the prediction information and combining the predicted samples with the prediction error.

Figure 13A:
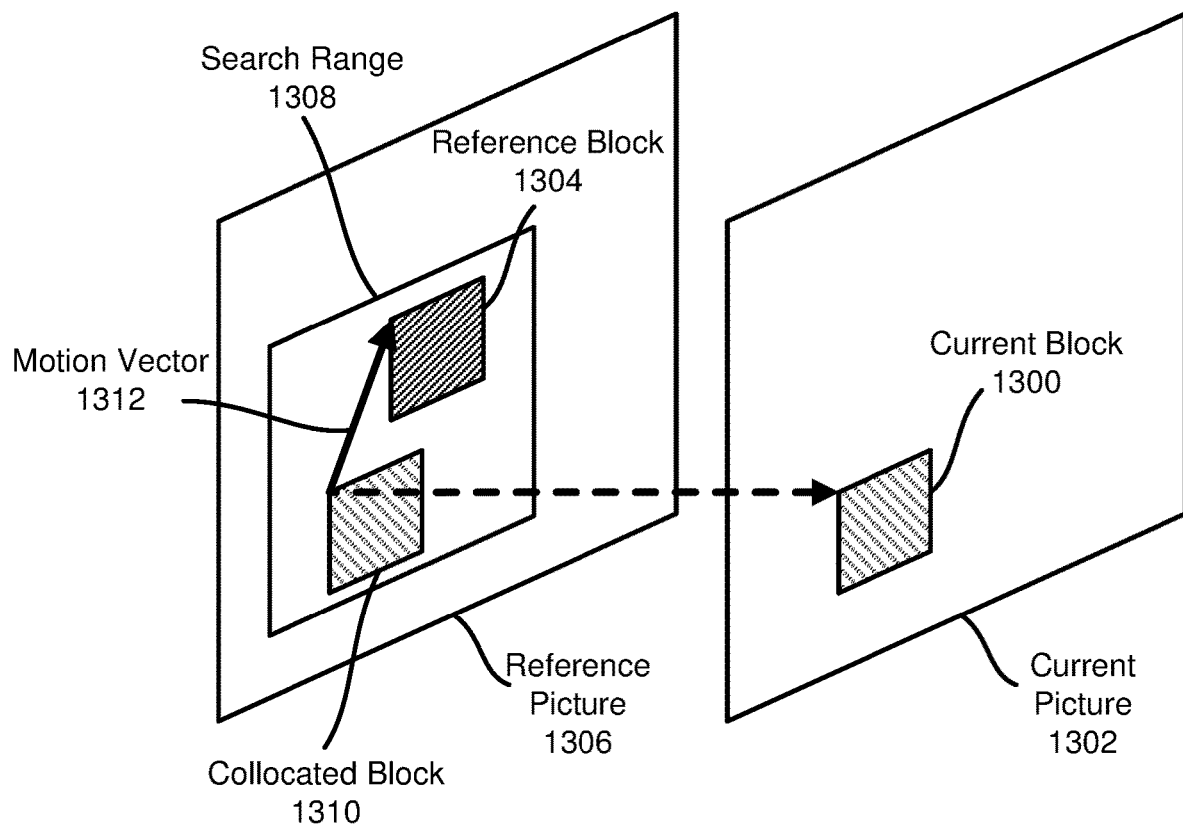
FIG. 13A illustrates an example of inter prediction performed for a current block in a current picture being encoded in accordance with embodiments of the present disclosure.

FIG. 13A illustrates an example of inter prediction performed for a current block 1300 in a current picture 1302 being encoded. An encoder, such as encoder 200 in FIG. 2, may perform inter prediction to determine and/or generate a reference block 1304 in a reference picture 1306 to predict current block 1300. Reference pictures, like reference picture 1306, are prior decoded pictures available at the encoder and decoder. Availability of a prior decoded picture may depend on whether the prior decoded picture is available in a decoded picture buffer at the time current block 1300 is being encoded or decoded. The encoder may, for example, search one or more reference pictures for a reference block that is similar to current block 1300. The encoder may determine a "best matching" reference block from the blocks tested during the searching process as reference block 1304. The encoder may determine that reference block 1304 is the best matching reference block based on one or more cost criterion, such as a rate-distortion criterion (e.g., Lagrangian rate-distortion cost). The one or more cost criterion may be based on, for example, a difference (e.g., sum of squared differences (SSD), sum of absolute differences (SAD), or sum of absolute transformed differences (SATD)) between the prediction samples of reference block 1304 and the original samples of current block 1300.

The encoder may search for reference block 1304 within a search range 1308. Search range 1308 may be positioned around the collocated position (or block) 1310 of current block 1300 in reference picture 1306. In some instances, search range 1308 may at least partially extend outside of reference picture 1306. When extending outside of reference picture 1306, constant boundary extension may be used such that the values of the samples in the row or column of reference picture 1306, immediately adjacent to the portion of search range 1308 extending outside of reference picture 1306, are used for the "sample" locations outside of reference picture 1306. All or a subset of potential positions within search range 1308 may be searched for reference block 1304. The encoder may utilize any one of a number of different search implementations to determine and/or generate reference block 1304. For example, the encoder may determine a set of a candidate search positions based on motion information of neighboring blocks to current block 1300.

One or more reference pictures may be searched by the encoder during inter prediction to determine and/or generate the best matching reference block. The reference pictures searched by the encoder may be included in one or more reference picture lists. For example, in HEVC and VVC, two reference picture lists may be used, a reference picture list 0 and a reference picture list 1. A reference picture list may include one or more pictures. Reference picture 1306 of reference block 1304 may be indicated by a reference index pointing into a reference picture list comprising reference picture 1306.

Figure 13B:
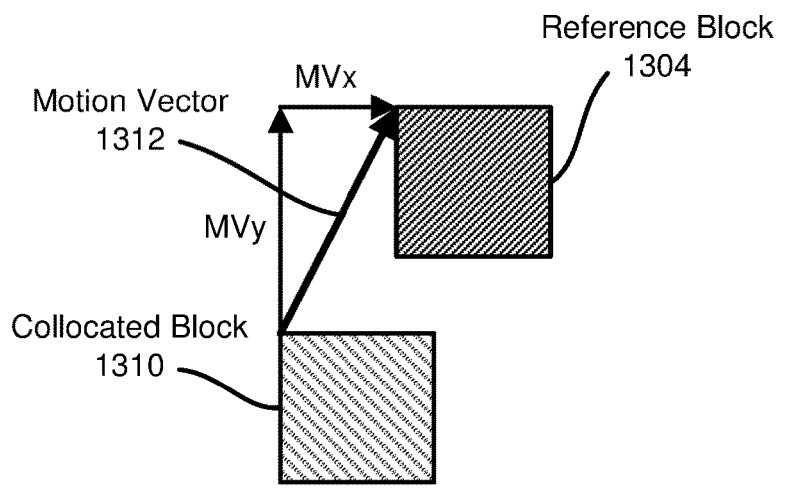
FIG. 13B illustrates an example horizontal component and vertical component of a motion vector in accordance with embodiments of the present disclosure.

The displacement between reference block 1304 and current block 1300 may be interpreted as an estimate of the motion between reference block 1304 and current block 1300 across their respective pictures. The displacement may be represented by a motion vector 1312. For example, motion vector 1312 may be indicated by a horizontal component ($MV_x$) and a vertical component ($MV_y$) relative to the position of current block 1300. FIG. 13B illustrates the horizontal component and vertical component of motion vector 1312. A motion vector, such as motion vector 1312, may have fractional or integer resolution. A motion vector with fractional resolution may point between two samples in a reference picture to provide a better estimation of the motion of current block 1300. For example, a motion vector may have ½, ¼, ⅛, ¹⁄₁₆, or ¹⁄₃₂ fractional sample resolution. When a motion vector points to a non-integer sample value in the reference picture, interpolation between samples at integer positions may be used to generate the reference block and its corresponding samples at fractional positions. The interpolation may be performed by a filter with two or more taps.

Once reference block 1304 is determined and/or generated for current block 1300 using inter prediction, the encoder may determine a difference (e.g., a corresponding sample-by-sample difference) between reference block 1304 and current block 1300. The difference may be referred to as a prediction error or residual. The encoder may then store and/or signal in a bitstream the prediction error and the related motion information for decoding or other forms of consumption. The motion information may include motion vector 1312 and a reference index pointing into a reference picture list comprising reference picture 1306. In other instances, the motion information may include an indication of motion vector 1312 and an indication of the reference index pointing into the reference picture list comprising reference picture 1306. A decoder may decode current block 1300 by determining and/or generating reference block 1304, which forms the prediction of current block 1300, using the motion information and combining the prediction with the prediction error.

Figure 14:
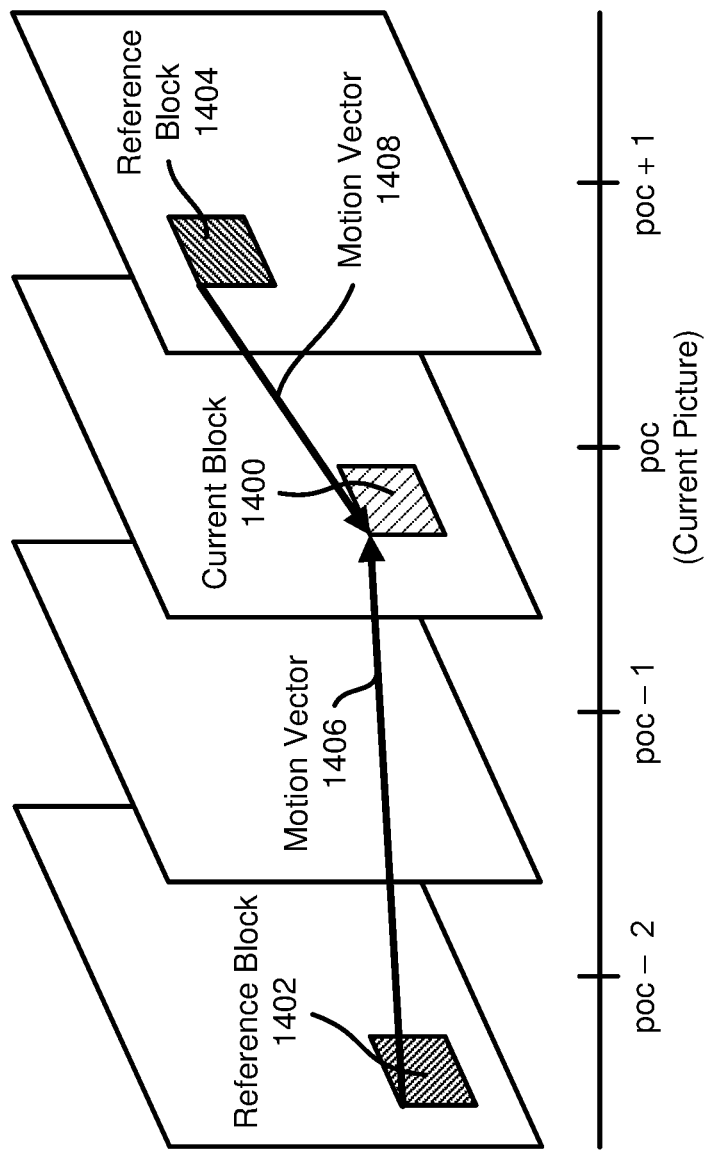
FIG. 14 illustrates an example of bi-prediction, performed for a current block in accordance with embodiments of the present disclosure.

In FIG. 13A, inter prediction is performed using one reference picture 1306 as the source of the prediction for current block 1300. Because the prediction for current block 1300 comes from a single picture, this type of inter prediction is referred to as uni-prediction. FIG. 14 illustrates another type of inter prediction, referred to as bi-prediction, performed for a current block 1400. In bi-prediction, the source of the prediction for a current block 1400 comes from two pictures. Bi-prediction may be useful, for example, where the video sequence comprises fast motion, camera panning or zooming, or scene changes. Bi-prediction may also be useful to capture fade outs of one scene or fade outs from one scene to another, where two pictures are effectively displayed simultaneously with different levels of intensity.

Whether uni-prediction or both uni-prediction and bi-prediction are available for performing inter prediction may depend on a slice type of current block 1400. For P slices, only uni-prediction may be available for performing inter prediction. For B slices, either uni-prediction or bi-prediction may be used. When uni-prediction is performed, an encoder may determine and/or generate a reference block for predicting current block 1400 from reference picture list 0. When bi-prediction is performed, an encoder may determine and/or generate a first reference block for predicting current block 1400 from reference picture list 0 and determine and/or generate a second reference block for predicting current block 1400 from reference picture list 1.

In FIG. 14, inter-prediction is performed using bi-prediction, where two reference blocks 1402 and 1404 are used to predict current block 1400. Reference block 1402 may be in a reference picture of one of reference picture list 0 or 1, and reference block 1404 may be in a reference picture of the other one of reference picture list 0 or 1. As shown in FIG. 14, reference block 1402 is in a picture that precedes the current picture of current block 1400 in terms of picture order count (POC), and reference block 1402 is in a picture that proceeds the current picture of current block 1400 in terms of POC. In other examples, the reference pictures may both precede or proceed the current picture in terms of POC. POC is the order in which pictures are output from, for example, a decoded picture buffer and is the order in which pictures are generally intended to be displayed. However, it should be noted that pictures that are output are not necessarily displayed but may undergo different processing or consumption, such as transcoding. In other examples, the two reference blocks determined and/or generated using bi-prediction may come from the same reference picture. In such an instance, the reference picture may be included in both reference picture list 0 and reference picture list 1.

A configurable weight and offset value may be applied to the one or more inter prediction reference blocks. An encoder may enable the use of weighted prediction using a flag in a picture parameter set (PPS) and signal the weighting and offset parameters in the slice segment header for the current block. Different weight and offset parameters may be signaled for luma and chroma components.

Once reference blocks 1402 and 1404 are determined and/or generated for current block 1400 using inter prediction, the encoder may determine a difference between current block 1400 and each of reference blocks 1402 and 1404. The differences may be referred to as prediction errors or residuals. The encoder may then store and/or signal in a bitstream the prediction errors and their respective related motion information for decoding or other forms of consumption. The motion information for reference block 1402 may include motion vector 1406 and the reference index pointing into the reference picture list comprising the reference picture of reference block 1402. In other instances, the motion information for reference block 1402 may include an indication of motion vector 1406 and an indication of the reference index pointing into the reference picture list comprising reference picture 1402. The motion information for reference block 1404 may include motion vector 1408 and the reference index pointing into the reference picture list comprising the reference picture of reference block 1404. In other instances, the motion information for reference block 1404 may include an indication of motion vector 1408 and an indication of the reference index pointing into the reference picture list comprising reference picture 1404. A decoder may decode current block 1400 by determining and/or generating reference blocks 1402 and 1404, which together form the prediction of current block 1400, using their respective motion information and combining the predictions with the prediction errors.

In HEVC, VVC, and other video compression schemes, motion information may be predictively coded before being stored or signaled in a bit stream. The motion information for a current block may be predictively coded based on the motion information of neighboring blocks of the current block. In general, the motion information of the neighboring blocks is often correlated with the motion information of the current block because the motion of an object represented in the current block is often the same or similar to the motion of objects in the neighboring blocks. Two of the motion information prediction techniques in HEVC and VVC include advanced motion vector prediction (AMVP) and inter prediction block merging.

An encoder, such as encoder 200 in FIG. 2, may code a motion vector using the AMVP tool as a difference between the motion vector of a current block being coded and a motion vector predictor (MVP). An encoder may select the MVP from a list of candidate MVPs. The candidate MVPs may come from previously decoded motion vectors of neighboring blocks in the current picture of the current block or blocks at or near the collocated position of the current block in other reference pictures. Both the encoder and decoder may generate or determine the list of candidate MVPs.

After the encoder selects an MVP from the list of candidate MVPs, the encoder may signal, in a bitstream, an indication of the selected MVP and a motion vector difference (MVD). The encoder may indicate the selected MVP in the bitstream by an index pointing into the list of candidate MVPs. The MVD may be calculated based on the difference between the motion vector of the current block and the selected MVP. For example, for a motion vector represented by a horizontal component ($MV_x$) and a vertical displacement ($MV_y$) relative to the position of the current block being coded, the MVD may be represented by two components calculated as follows:

$$MVD_x = MV_x - MVP_x \quad (10)$$

$$MVD_y = MV_y - MVP_y \quad (11)$$

where $MVD_x$ and $MVD_y$ respectively represent the horizontal and vertical components of the MVD, and $MVP_x$ and $MVP_y$ respectively represent the horizontal and vertical components of the MVP. A decoder, such as decoder 300 in FIG. 3, may decode the motion vector by adding the MVD to the MVP indicated in the bitstream. The decoder may then decode the current block by determining and/or generating the reference block, which forms the prediction of the current block, using the decoded motion vector and combining the prediction with the prediction error.

Figure 15A:
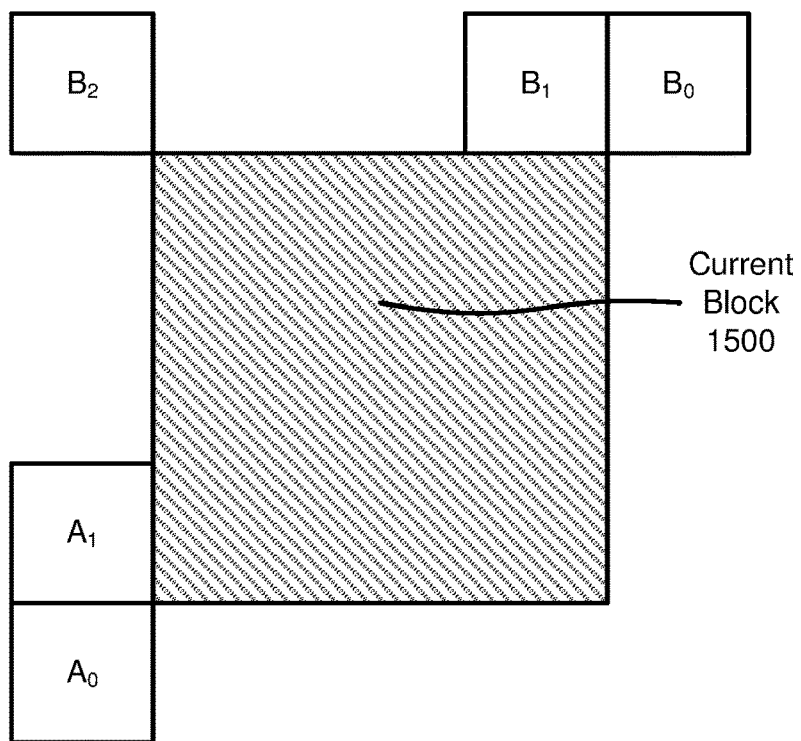
FIG. 15A illustrates an example location of five spatial candidate neighboring blocks relative to a current block being coded in accordance with embodiments of the present disclosure.
Figure 15B:
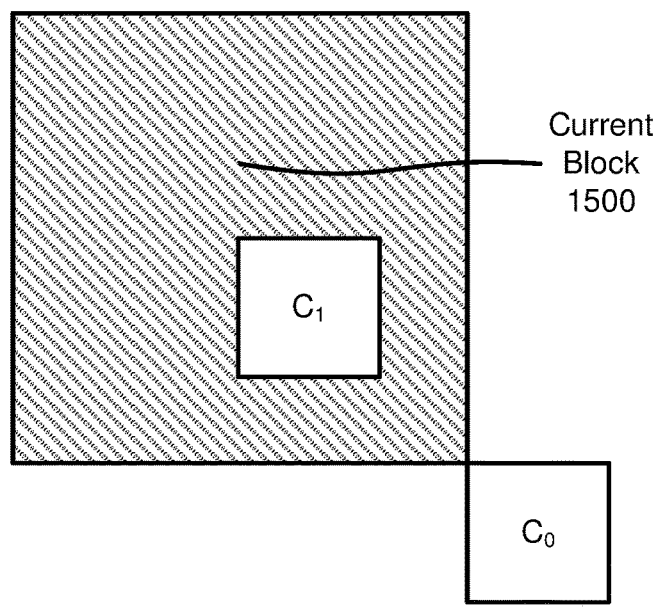
FIG. 15B illustrates an example location of two temporal, co-located blocks relative to a current block being coded in accordance with embodiments of the present disclosure.

In HEVC and VVC, the list of candidate MVPs for AMVP may comprise two candidates referred to as candidates A and B. Candidates A and B may include up to two spatial candidate MVPs derived from five spatial neighboring blocks of the current block being coded, one temporal candidate MVP derived from two temporal, co-located blocks when both spatial candidate MVPs are not available or are identical, or zero motion vectors when the spatial, temporal, or both candidates are not available. FIG. 15A illustrates the location of the five spatial candidate neighboring blocks relative to a current block 1500 being encoded. The five spatial candidate neighboring blocks are respectively denoted $A_0$, $A_1$, $B_0$, $B_1$, and $B_2$. FIG. 15B illustrates the location of the two temporal, co-located blocks relative to current block 1500 being coded. The two temporal, co-located blocks are denoted $C_0$ and $C_1$ and are included in a reference picture that is different from the current picture of current block 1500.

An encoder, such as encoder 200 in FIG. 2, may code a motion vector using the inter prediction block merging tool also referred to as merge mode. Using merge mode, the encoder may reuse the same motion information of a neighboring block for inter prediction of a current block. Because the same motion information of a neighboring block is used, no MVD needs to be signaled and the signaling overhead for signaling the motion information of the current block may be small in size. Similar to AMVP, both the encoder and decoder may generate a candidate list of motion information from neighboring blocks of the current block. The encoder may then determine to use (or inherit) the motion information of one neighboring block's motion information in the candidate list for predicting the motion information of the current block being coded. The encoder may signal, in the bit stream, an indication of the determined motion information from the candidate list. For example, the encoder may signal an index pointing into the list of candidate motion information to indicate the determined motion information.

In HEVC and VVC, the list of candidate motion information for merge mode may comprise up to four spatial merge candidates that are derived from the five spatial neighboring blocks used in AMVP as shown in FIG. 15A, one temporal merge candidate derived from two temporal, co-located blocks used in AMVP as shown in FIG. 15B, and additional merge candidates including bi-predictive candidates and zero motion vector candidates.

It should be noted that inter prediction may be performed in other ways and variants than those described above. For example, motion information prediction techniques other than AMVP and merge mode are possible. In addition, although the description above was primarily made with respect to inter prediction modes in HEVC and VVC, it will be understood that the techniques of the present disclosure described above and further below may be applied to other inter prediction modes, including those of other video coding standards like VP8, VP9, AV1, and the like. In addition, history based motion vector prediction (HMVP), combined intra/inter prediction mode (CIIP), and merge mode with motion vector difference (MMVD) as described in VVC may also be performed and are within the scope of the present disclosure.

In inter prediction, a block matching technique may be applied to determine a reference block in a different picture than the current block being encoded. Block matching techniques have also been applied to determine a reference block in the same picture as a current block being encoded. However, it has been determined that for camera-captured videos, a reference block in the same picture as the current block determined using block matching may often not accurately predict the current block. For screen content video this is generally not the case. Screen content video may include, for example, computer generated text, graphics, and animation. Within screen content, there is often repeated patterns (e.g., repeated patterns of text and graphics) within the same picture. Therefore, a block matching technique applied to determine a reference block in the same picture as a current block being encoded may provide efficient compression for screen content video.

HEVC and VVC both include a prediction technique to exploit the correlation between blocks of samples within the same picture of screen content video. This technique is referred to as intra block copy (IBC) or current picture referencing (CPR). Similar to inter prediction, an encoder may apply a block matching technique to determine a displacement vector (referred to as a block vector (BV)) that indicates the relative displacement from the current block to a reference block (or intra block compensated prediction) that "best matches" the current block. The encoder may determine the best matching reference block from blocks tested during a searching process similar to inter prediction. The encoder may determine that a reference block is the best matching reference block based on one or more cost criterion, such as a rate-distortion criterion (e.g., Lagrangian rate-distortion cost). The one or more cost criterion may be based on, for example, a difference (e.g., sum of squared differences (SSD), sum of absolute differences (SAD), sum of absolute transformed differences (SATD), or difference determined based on a hash function) between the prediction samples of the reference block and the original samples of the current block. A reference block may correspond to prior decoded blocks of samples of the current picture. The reference block may comprise decoded blocks of samples of the current picture prior to being processed by in-loop filtering operations, like deblocking or SAO filtering. FIG. 16 illustrates an example of IBC applied for screen content. The rectangular portions with arrows beginning at their boundaries are current blocks being encoded and the rectangular portions that the arrows point to are the reference blocks for predicting the current blocks.

Once a reference block is determined and/or generated for a current block using IBC, the encoder may determine a difference (e.g., a corresponding sample-by-sample difference) between the reference block and the current block. The difference may be referred to as a prediction error or residual. The encoder may then store and/or signal in a bitstream the prediction error and the related prediction information for decoding or other forms of consumption. The prediction information may include a BV. In other instances, the prediction information may include an indication of the BV. A decoder, such as decoder 300 in FIG. 3, may decode the current block by determining and/or generating the reference block, which forms the prediction of the current block, using the prediction information and combining the prediction with the prediction error.

In HEVC, VVC, and other video compression schemes, a BV may be predictively coded before being stored or signaled in a bit stream. The BV for a current block may be predictively coded based on the BV of neighboring blocks of the current block. For example, an encoder may predictively code a BV using the merge mode as explained above for inter prediction or a similar technique as AMVP also explained above for inter prediction. The technique similar to AMVP may be referred to as BV prediction and difference coding.

For BV prediction and difference coding, an encoder, such as encoder 200 in FIG. 2, may code a BV as a difference between the BV of a current block being coded and a BV predictor (BVP). An encoder may select the BVP from a list of candidate BVPs. The candidate BVPs may come from previously decoded BVs of neighboring blocks of the current block in the current picture. Both the encoder and decoder may generate or determine the list of candidate BVPs.

After the encoder selects a BVP from the list of candidate BVPs, the encoder may signal, in a bitstream, an indication of the selected BVP and a BV difference (BVD). The encoder may indicate the selected BVP in the bitstream by an index pointing into the list of candidate BVPs. The BVD may be calculated based on the difference between the BV of the current block and the selected BVP. For example, for a BV represented by a horizontal component (BVx) and a vertical component (BVy) relative to the position of the current block being coded, the BVD may represented by two components calculated as follows:

$$BVD_x = BV_x - BVP_x \quad (12)$$

$$BVD_y = BV_y - BVP_y \quad (13)$$

where BVDx and BVDy respectively represent the horizontal and vertical components of the BVD, and BVPx and BVPy respectively represent the horizontal and vertical components of the BVP. A decoder, such as decoder 300 in FIG. 3, may decode the BV by adding the BVD to the BVP indicated in the bitstream. The decoder may then decode the current block by determining and/or generating the reference block, which forms the prediction of the current block, using the decoded BV and combining the prediction with the prediction error.

In HEVC and VVC, the list of candidate BVPs may comprise two candidates referred to as candidates A and B. Candidates A and B may include up to two spatial candidate BVPs derived from five spatial neighboring blocks of the current block being encoded, or one or more of the last two coded BVs when spatial neighboring candidates are not available (e.g., because they are coded in intra or inter mode). The location of the five spatial candidate neighboring blocks relative to a current block being encoded using IBC are the same as those shown in FIG. 15A for inter prediction. The five spatial candidate neighboring blocks are respectively denoted A0, A1, B0, B1, and B2.

Figure 17:
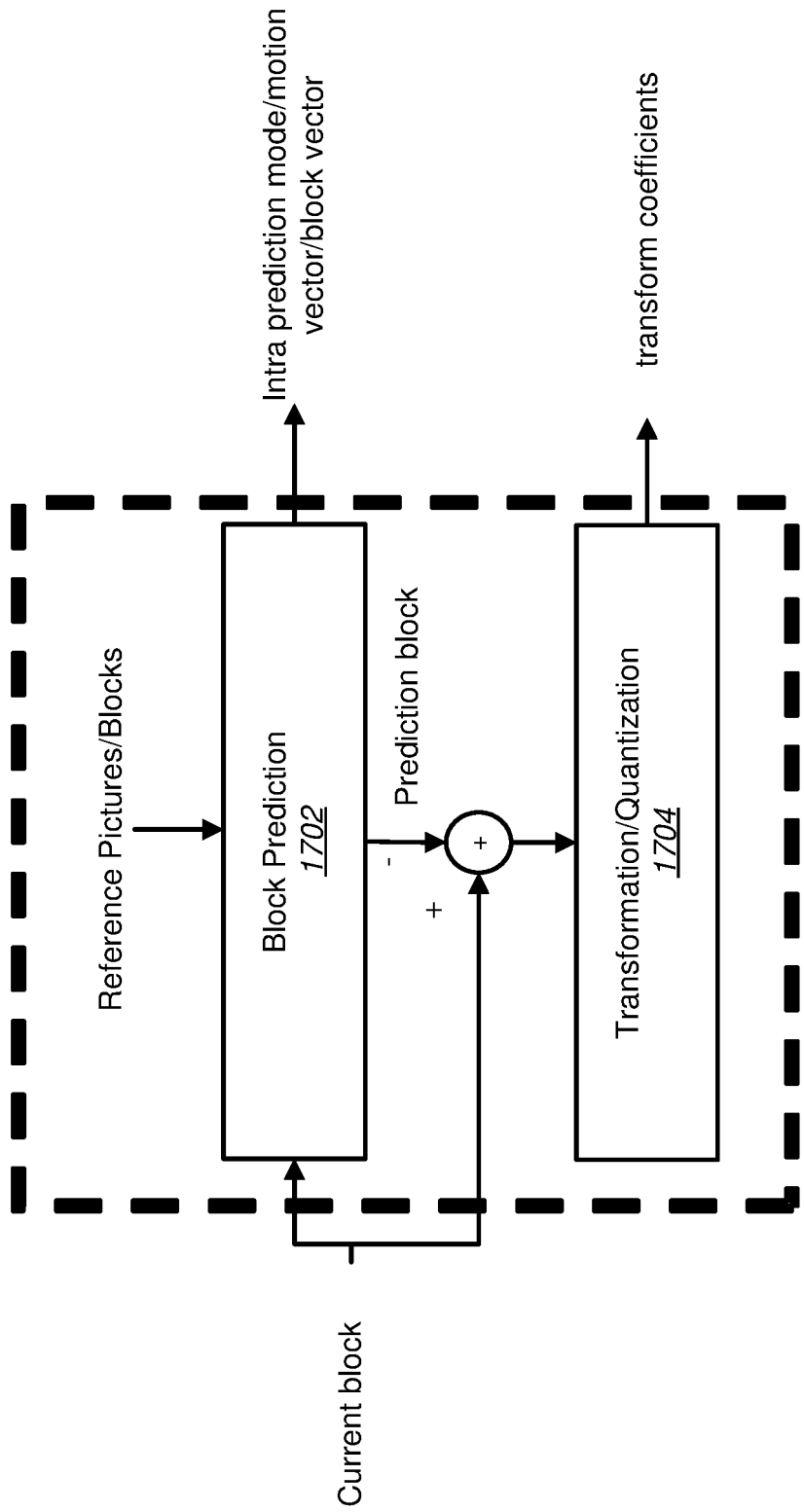
FIG. 17 illustrates an example of block prediction based block encoding.

In H.264, there may be two different block predictions such as inter prediction and intra prediction. HEVC and VVC may include intra block copy prediction. FIG. 17 shows an example of a block prediction based block encoding. A current block is a block being encoded.

At 1702, a prediction block for the current block may be estimated using block prediction based on reference pictures/blocks. Reference pictures/blocks may be decoded pictures/blocks stored in a buffer (for example unit 222 in FIG. 2) in the encoder before encoding the current block.

In intra prediction, a prediction block includes predicted samples of the current block using a selected intra prediction mode. In intra prediction, the encoder may generate the prediction block of the current block based on a plurality of intra prediction modes. For example, the encoder may generate prediction block for each of the 35 intra prediction modes in HEVC or 67 intra prediction modes in VVC. The encoder may apply each of the intra prediction modes to the current block. For each intra prediction mode applied, the encoder may determine a prediction error for the current block based on a difference (e.g., sum of squared differences (SSD), sum of absolute differences (SAD), or sum of absolute transformed differences (SATD)) between the prediction samples determined for the intra prediction mode and the original samples of the current block. The encoder may select one of the intra prediction modes to encode the current block based on the determined prediction errors. For example, the encoder may select an intra prediction mode that results in the smallest prediction error for the current block. In an example, the encoder may select the intra prediction mode to encode the current block based on a rate-distortion measure (e.g., Lagrangian rate-distortion cost) determined using the prediction errors.

In inter prediction, an encoder determines and/or generate a reference block in a reference pictures (or reconstructed pictures) to predict current block, for example, as explained in FIG. 13. For example, the encoder may determine a best matching reference block based on one or more cost criterion, such as a rate-distortion criterion (e.g., Lagrangian rate-distortion cost). For example, a best matching reference block is a reference block in a plurality of blocks of a picture that has the lowest cost (e.g. rate-distortion cost) among the plurality of blocks of the picture. The one or more cost criterion may be based on, for example, a difference (e.g., sum of squared differences (SSD), sum of absolute differences (SAD), or sum of absolute transformed differences (SATD)) between the samples of reference block and the original samples of current block. A motion vector directing the best matching reference block from the current block may be signaled to decoder and used for generating motion compensated prediction block. In inter prediction, the prediction block may be the best matching reference block.

In intra block copy prediction, an encoder determines and/or generate a reference block in a reference blocks (or reconstructed blocks) in the same picture of the current block to predict current block as explained in FIG. 16. The encoder may determine a best matching reference block based on one or more cost criterion, such as a rate-distortion criterion (e.g., Lagrangian rate-distortion cost). The one or more cost criterion may be based on, for example, a difference (e.g., sum of squared differences (SSD), sum of absolute differences (SAD), or sum of absolute transformed differences (SATD)) between the samples of reference block and the original samples of current block. A block vector directing the best matching reference block from the current block may be signaled to decoder and used for generating block vector compensated prediction block. In intra block copy prediction, the prediction block is the best matching reference block.

At 1704, a residual block (also referred to as a prediction error) determined based on the difference between the current block and the prediction block may be compressed into transform coefficients (or residual coefficients) by applying s transform and quantization, for example, as explained above with respect to FIG. 2.

The intra prediction mode/motion vector/block vector and transform coefficients are additionally compressed by entropy coding, for example, as explained above with respect to FIG. 2. Context-based adaptive variable length coding (CAVLC) may be entropy coding method employed in the H.264/AVC standard. Context-based adaptive binary arithmetic coding (CABAC) is employed in H.264/AVC, HEVC, and VVC.

Figure 18:
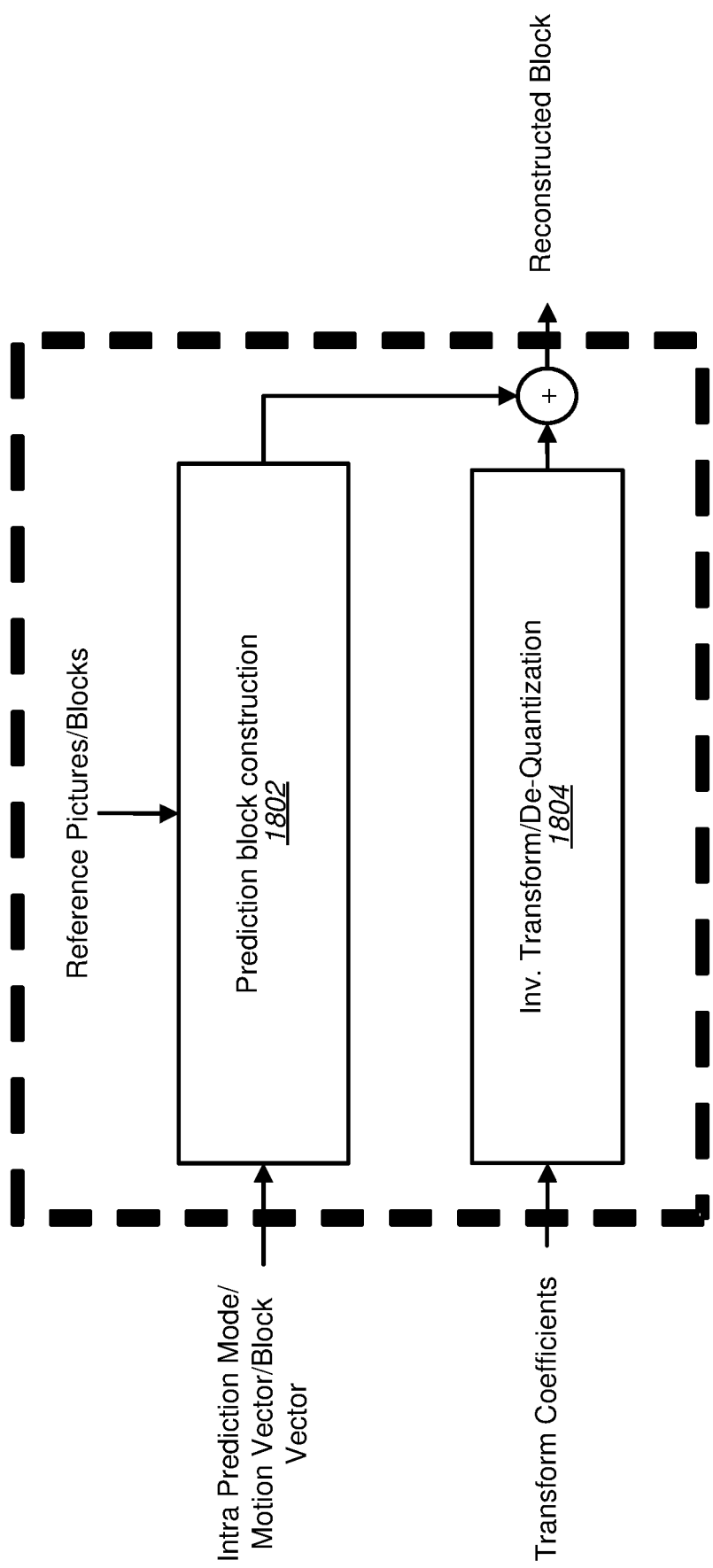
FIG. 18 illustrates an example of block prediction based block decoding.

FIG. 18 shows an example of a block prediction based block decoding. A block being decoded (or current block) may be read from a bit stream (encoded video) and decoded by the block prediction based block decoding. A reference pictures/blocks may be decoded pictures/blocks stored in a buffer (for example as unit 314 in FIG. 3) in the decoder before decoding the current block. A reconstructed block is a decoded sample of the current block. The decoder decodes intra prediction mode/motion vector/block vector and transform coefficients of the current block by performing entropy decoding the corresponding bits in the bit stream. A block prediction based block decoding may receive the intra prediction mode/motion vector/block vector and the transform coefficients to reconstruct the current block.

Block 1802 may generate a prediction block of the current block, for example, by intra prediction unit 318 or inter prediction unit 316 in FIG. 3. An intra prediction compensated block, a motion compensated block, or a block vector compensated block may be examples of prediction blocks. In an example, intra prediction mode in intra prediction may be depicted in FIG. 10A, and FIG. 10B. In an example, motion vector of inter prediction may be depicted in FIG. 13B. In an example, block vector of intra block copy may be depicted in FIG. 16. In intra prediction, the prediction block is predicted samples of the current block using the decoded intra prediction mode. In inter prediction and intra block copy, the prediction block is a reference block directed by the decoded motion vector or the decoded block vector.

At 1804, a reconstructed residual block may be generated by applying de-quantization and inverse transform to the transform coefficients, for example, which may be performed at unit 308 in FIG. 3.

Finally, the reconstructed block of the current block may be generated by summation of the prediction block and the reconstructed residual block.

In existing technologies, an encoder may signal an intra prediction mode selected to encode a block using a fixed-length binarization of the mode index. The fixed-length binarization of an unsigned integer x, where $0 \leq x < M$, is given by its binary representation of length $\lceil \log_2 M \rceil$ bits. For example, an encoder may signal the intra prediction mode selected among the 35 intra prediction modes in HEVC to encode a block using a fixed-length binarization of the mode index. With 35 different intra prediction modes available, the fixed-length binarization of the mode index requires 6-bits. This signaling overhead reduces the compression gain achieved by removing redundant information for a block based on the selected intra prediction mode. In newer video coding standards, the reduction in compression gain may be further reduced by support for a larger number of intra prediction modes and overall better compression gains. For example, in VVC, the successor to HEVC, 67 intra prediction modes are supported. With 67 different intra prediction modes available, the fixed-length binarization of the mode index requires 7-bits. In some video coding standards, like HEVC and VVC, a smaller list of most probable modes (MPMs) may be constructed at an encoder and decoder to reduce intra prediction mode signaling overhead. If a selected intra prediction mode is within the MPM list, an encoder may signal the selected intra prediction mode using a smaller number of bits (e.g., 2 or 3 bits) based on the smaller size of the MPM list. However, even with the use of the MPM list, an encoder may often have to fall back to signaling a selected intra-prediction mode using a fixed-length binarization of the mode index based on the selected mode not being in the MPM list.

Embodiments of the present disclosure are related to an approach for reducing the overhead of signaling an intra prediction mode selected by, for example, an encoder to encode a current block. Embodiments of the present disclosure may perform a no reference image quality assessment of a block to more efficiently signal the selected intra prediction mode. For example, embodiments of the present disclosure may generate a prediction of the selected intra prediction mode at the encoder and decoder using a no reference image quality assessment of a block. The encoder may then signal the selected intra prediction, based on the prediction, in a more efficient manner to the decoder. These and other features of the present disclosure are described further below.

Figure 19:
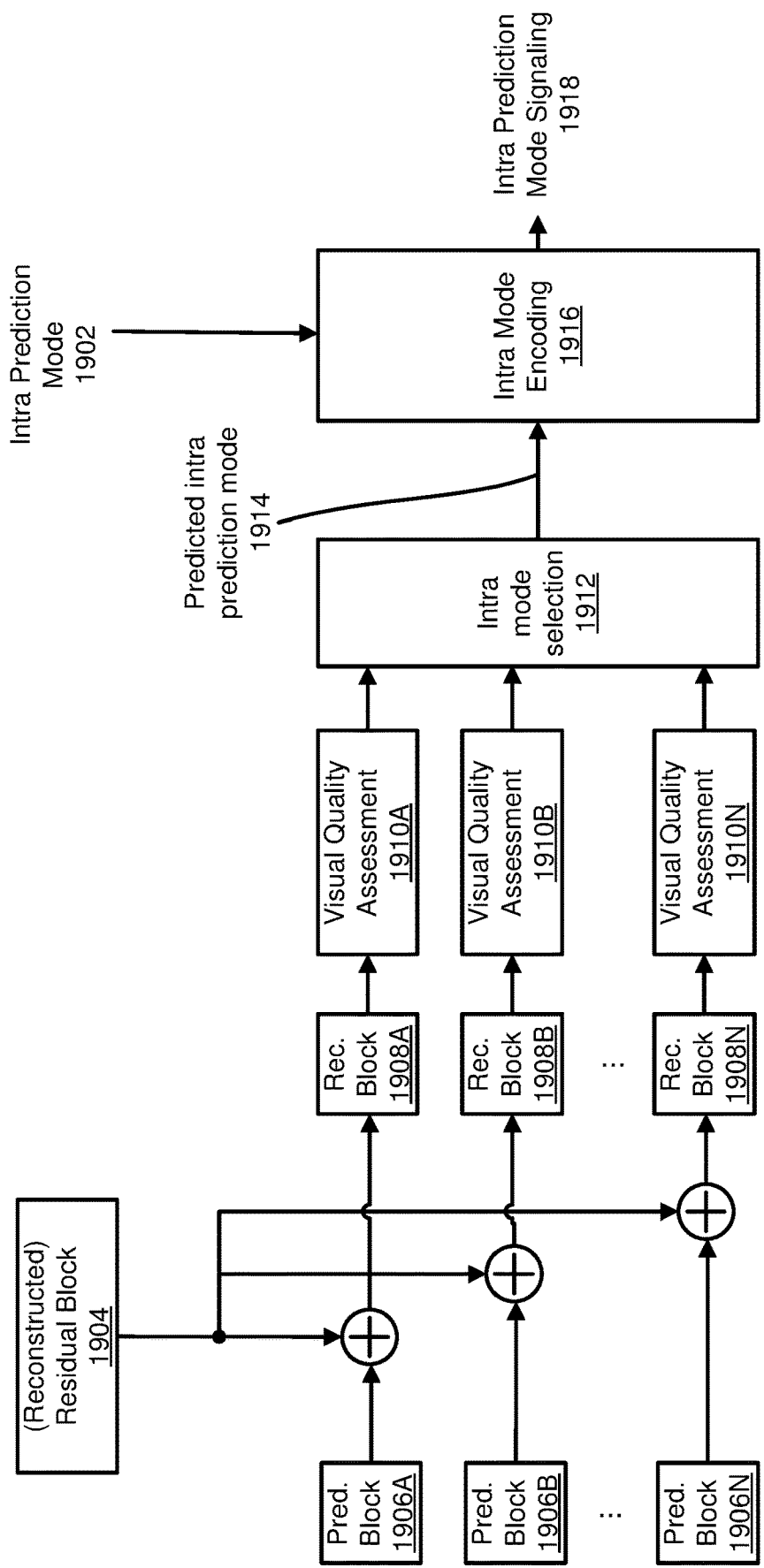
FIG. 19 illustrates an example of the prediction of intra prediction mode in both encoder side and decoder side.

FIG. 19 illustrates an example of generating a prediction of a selected intra prediction mode using an no reference image quality assessment to reduce overhead of signaling the selected intra prediction mode in accordance with embodiments of the present disclosure. The example of FIG. 19 may be performed after an encoder has performed (or while the encoder is performing) intra prediction for a current block. As part of the intra prediction process, the encoder may select an intra prediction mode 1902, from among a plurality of intra prediction modes, to encode the current block. For example, the encoder may predict the samples of the current block for each of the 35 intra prediction modes in HEVC or 67 intra prediction modes in VVC as explained above with respect to FIGS. 9-12. For each intra prediction mode applied, the encoder may determine a prediction error for the current block based on a difference (e.g., sum of squared differences (SSD), sum of absolute differences (SAD), or sum of absolute transformed differences (SATD)) between the prediction samples determined for the intra prediction mode and the original samples of the current block. The encoder may select intra prediction mode 1902 from the plurality of intra prediction modes to encode the current block based on the determined prediction errors. For example, the encoder may select intra prediction mode 1902 based on intra prediction mode 1902 resulting in the smallest prediction error for the current block. In another example, the encoder may select intra prediction mode 1902 to encode the current block based on a rate-distortion measure determined using the prediction errors.

The encoder may send an indication of selected intra prediction mode 1902 and its corresponding prediction error or residual block 1904 to a decoder for decoding of the current block. However, directly signaling selected intra prediction mode 1902 to a decoder may significantly reduce the compression gain achieved by intra prediction of the current block. To reduce the overhead of signaling selected intra prediction mode 1902 to a decoder, the encoder may determine a prediction of selected intra prediction mode 1902 and use the prediction to more efficiently signal selected intra prediction mode 1902. The prediction method may be performed using information already available at a decoder (e.g., based on traditional intra prediction schemes) to limit signaling overhead.

For example, to generate the prediction of selected intra prediction mode 1902, the encoder may generate a series of reconstructed versions of the current block. Each of the reconstructed version of the current block may be based on residual block 1904 and a respective prediction generated for a different one of a plurality of intra prediction modes. For example, the encoder may generate each of the reconstructed versions of the current block based on a sum of residual block 1904 and a respective prediction of the current block generated for a different one of a plurality of intra prediction modes. The version of the current block reconstructed using residual block 1904 and the prediction generated using selected intra prediction mode 1902 should, in general or typically, provide the "best" reconstructed version of the current block given that residual block 1904 was determined on the basis of this prediction. The encoder may perform a respective quality assessment on each of the reconstructed versions of the current block with a no reference image quality assessment. The encoder may then encode selected intra prediction mode 1902 for signaling to the decoder based on the respective quality assessments.

For example, as shown in FIG. 19, the encoder may generate one or more prediction blocks 1906A-1906N for the current block being encoded. Each of the one or more prediction blocks 1906A-1906N may correspond to a prediction of the current block generated based a different intra prediction mode. For example, the encoder may generate a prediction block 1906 for each intra prediction mode tested by the encoder when determining selected intra prediction mode 1902, including selected intra prediction mode 1902 itself. In another example, the encoder may generate a prediction block 1906 for each intra prediction mode available at the decoder for decoding the current block. In one example, the encoder may generate prediction blocks 1906A-1906N as part of the intra prediction performed on the current block to determine selected intra prediction mode 1902.

After generating the one more prediction blocks 1906A-1906N, the encoder may add residual block 1904 to each prediction block 1906A-1906N (e.g., by performing a corresponding sample-by-sample addition). In one example, the encoder may add a reconstructed version of residual block (or reconstructed residual block) 1904, which is available at a decoder, to each prediction block 1906A-1906N. For example, the encoder may determine the reconstructed residual block 1904 by performing one or more of an inverse transformation and inverse quantization on a coded version of residual block 1904 sent to the decoder. The encoder may add residual block 1904 (or reconstructed residual block 1904) and the respective prediction block 1906 to each prediction block 1906A-1906N to generate a series of reconstructed blocks 1908A-1908N.

The encoder may perform visual quality assessments 1910A-1910N on reconstructed block 1908A-1908N. Visual quality assessments 1910A-1910N may be performed to assess the quality of each reconstructed block 1908 as compared to the current block being encoded without using the current block as a reference. For example, visual quality assessments 1910A-1910N may be performed by a no reference image quality assessment that does not use the current, unencoded block as a reference. For example, the no reference image quality assessment may be based on a visual parameter measurement index (VPMI) and/or a deep Learning for Blind Image Quality Assessment (DeepBIQ) as explained further below. Because visual quality assessments 1910A-1910N are performed without using the current, unencoded block as reference by which to measure quality, the decoder may perform the same assessment without receiving additional information from the encoder.

Intra mode selection 1912 may determine a predicted intra prediction mode 1914 using the quality metric of each visual quality assessment 1910A-1910N. For example, the prediction mode corresponding to the reconstructed block, among reconstructed blocks 1908A-1908N, with the highest determined visual quality metric may be determined as the predicted intra prediction mode 1914.

The encoder may perform intra mode encoding 1916 using predicted intra prediction mode 1914 and selected intra prediction mode 1902. For example, if predicted intra prediction mode 1914 is the same intra prediction mode as selected intra prediction mode 1902, the encoder may encode selected intra prediction mode 1902 using one or more fewer bits than used to signal a fixed-length binarization of selected intra prediction mode 1902. In an embodiment, the encoder may signal selected intra prediction mode 1902 to a decoder using a single, one-bit flag based on the above condition based on predicted intra prediction mode 1914 being the same intra prediction mode as selected intra prediction mode 1902.

In an example, based on predicted intra prediction mode 1914 being different than selected intra prediction mode 1902, the encoder may signal to a decoder an indication that predicted intra prediction mode 1914 and selected intra prediction mode 1902 are different. For example, the encoder may use the same single, one-bit flag to provide such an indication. The encoder may fall back to signaling selected intra prediction mode 1902 using a fixed-length binarization of the index of selected intra prediction mode 1902. In other example, based on predicted intra prediction mode 1914 being different than selected intra prediction mode 1902, the encoder may signal to a decoder a difference between intra prediction mode 1902 and predicted intra prediction mode 1914.

The decoder may decode selected intra prediction mode 1902 based on the signaling from the encoder and the decoder's own independent determination of predicted intra prediction mode 1914. For example, if the decoder receives intra prediction mode signaling 1918 indicating that intra prediction mode 1902 is the same as predicted intra prediction mode 1914 (e.g., based on the value of a one-bit flag), the decoder may independently determine prediction blocks 1906A-1906N, reconstructed blocks 1908A-1908N, visual quality assessments 1910A-1910N and, ultimately, the estimated intra prediction mode 1914. The decoder may then perform intra prediction using predicted intra prediction mode 1914 to decode the current block without receiving intra prediction mode 1902 from the encoder If the decoder receives intra prediction mode signaling 1918 indicating that intra prediction mode 1902 is not the same as predicted intra prediction mode 1914 (e.g., based on the value of a one-bit flag), the decoder may receive the selected intra prediction mode 1902 from the encoder and perform intra prediction using the selected intra prediction mode 1902. In this case, the decoder may not perform any independent determination of the estimated intra prediction mode 1914.

Figure 20:
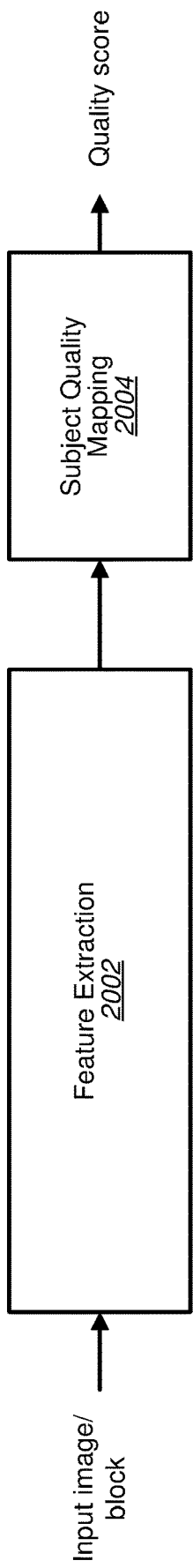
FIG. 20 illustrates an example of no reference image quality assessment.

FIG. 20 illustrates an example of a no reference image quality assessment in accordance with embodiments of the present disclosure. The example of FIG. 20 may be used to implement visual quality assessments 1910A-1910N in FIG. 19. The example shown in FIG. 20 comprises a feature extraction 2002 and a subject quality mapping 2004.

Feature extraction 2002 may extract, features from an input image or at least one input image block. Examples of the features may include raw pixels, outputs of filters such as Gabor and edge detector, or outputs of transforms such as DCT and Wavelet.

Subject quality mapping 2004 may receive the extracted features from feature extraction 2002 and input the extracted features into an image quality prediction model. The image quality prediction model may predict a visual quality score of the input image/block. In an example, the image quality prediction model may be constructed by training of machine learning methods. Examples of machine learning methods may include linear regression, support vector machine (SVM), decision tree, and/or deep neural network (DNN). In an example, the image quality prediction model may be based on an equation that may receive the feature values and outputs the visual quality value. the equational representation may be, for example, a visual parameter measurement index (VPMI).

Figure 21:
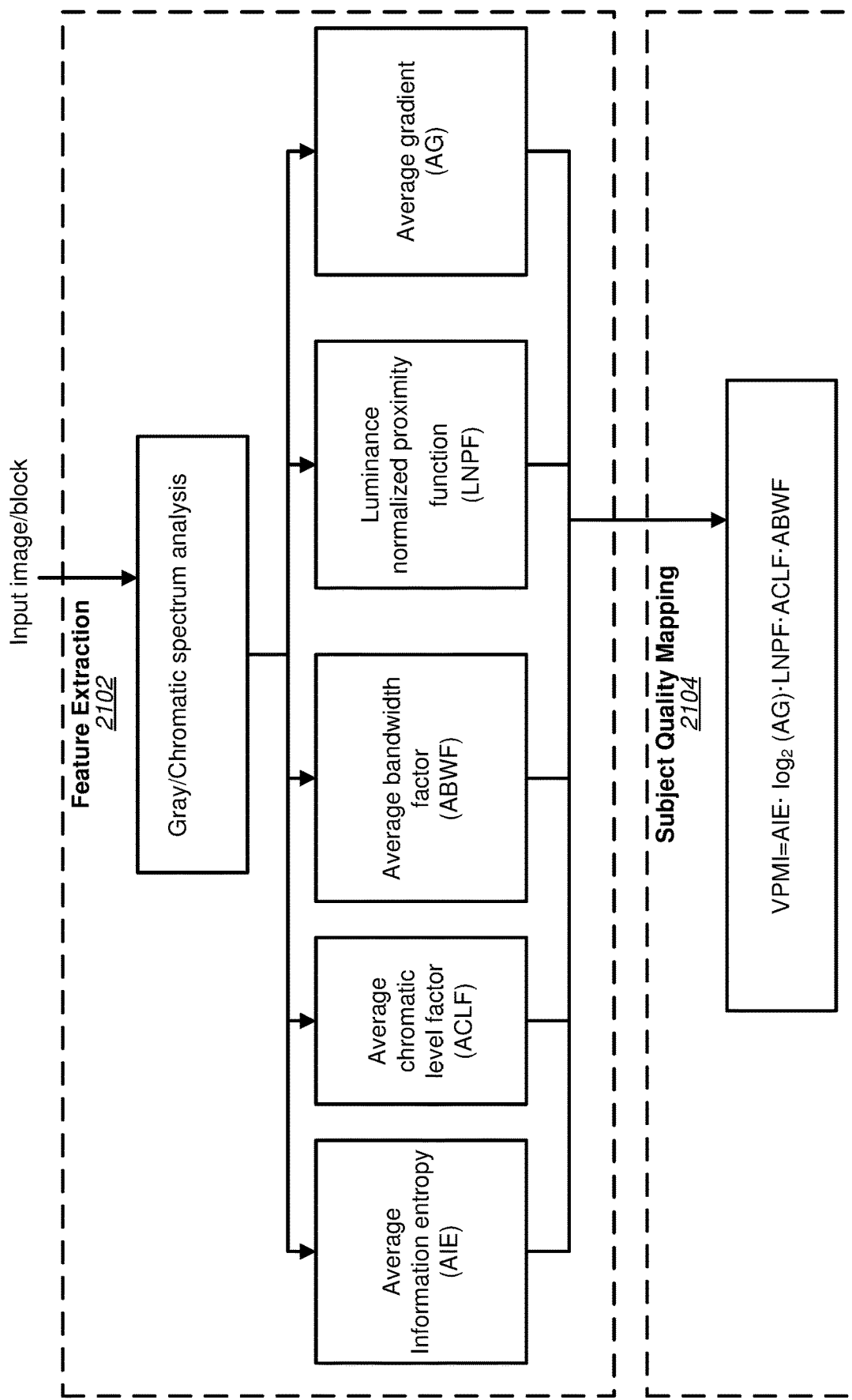
FIG. 21 illustrates an example of no reference image quality assessment based on visual parameter measurement index (VPMI).

FIG. 21 illustrates an example of a no reference image quality assessment based on visual parameter measurement index (VPMI). VPMI is based on integration of visual metrics to assess image quality. In an example, the maximum of VPMI may correspond to the best quality of the color image. The features comprising the most basic characteristics for constructing an image may influence the visual quality of an image.

The primary and fundamental parameters may be the luminance, information entropy, contrast, and so on. These metrics may be physical quantities. The quality of an image may be described based on a luminance not too bright or too dark, an amount of image information, a contrast, an amount of color components, and/or a bandwidth. The metrics, for example, average information entropy, average chromatic level factor, average gradient, average luminance, and/or average bandwidth factor may be used as one or more features, for example, as visual perception parameters, which may be measured and transformed into a mathematical model.

VPMI may comprise gray/chromatic spectrum analysis, visual parameters measurement, and/or comprehensive image quality assessment function.

Feature extraction 2102 may extract feature of an input image/block. For example, feature extraction 2102 may extract one or more of average information entropy (AIE), average chromatic level factor (ACLF), average bandwidth factor (ABWF), average luminance (AL), and/or average gradient (AG).

In an example, to calculate the one or more features, gray/chromatic spectrum analysis may be performed to obtain the distribution of the pixel number with the gray/chromatic level of the image. In an example, visual parameters measurement may measure five basic metrics that are relative to the image quality.

Average information entropy (AIE) may reflect the quantity of information. Quality of an image may be proportional to information in the image. For example, an image with relatively good quality may possess some image information. Average information entropy (AIE) may be calculated as a root of average of squared entropy of each color component.

The average chroma level factor (ACLF) may be calculated as a root of average of squared color component's chromatic level factors (CLF): The CLF(n), represents the complex of chromatic level of n-th color component for an image. The maximal value of the chromatic spectrum of each color component may be equal to 256. In an example, the maximal value may be a percentage and the maximum may be equal to one from CLF. In an example, a greater ACLF may correspond to a better image quality.

In an example embodiment, the normalized bandwidth of the gray/chromatic spectrum of an image may be referred to as the bandwidth factor (BWF). The average bandwidth of the gray/chromatic spectrum of an image (ABWF) may be computed as a root of average of squared band width factor (BWF) of each color component. The BWF may be calculated as $$BWF(n)=(Right(n)-Left(n)+1)/256 \quad (14)$$

where, BWF(n) may be the normalized bandwidth of the nth color channel. Right(n) and Left(n) may be referred to as the right boundary and left boundary values of the nth color channel, respectively.

Average luminance (AL) for an image may be computed as a root of average of each color component's average luminance. Luminance normalized proximity function (LNCF) may be calculated as $$LNCF=1-abs(AL-ALop)/ALop \quad (15)$$

where abs(•) may be the absolute operator. ALop may be the optimal average luminance and ALop value may be equal to 127.5. When AL=ALop, LNPF=1, which may indicate that the luminance of the image may be optimized for 127.5 and may correspond to the best visual image for the same image. LNPF may represent the deviation of AL to ALop.

Average gradient (AG) may represent the visibility and clarity of the image. The image gradient may be a factor for the visual perception characteristics. In an example, according to Weber-Fechner's law in relative contrast sensitivity experiments, the brightness information that the human eye observes may be limited. The law may not be suitable for dark vision. AG may be computed as a root of average of each color component's squared gradient.

At 2104, visual quality score may be calculated as VPMI. The basic visual metrics comprise the important elements for constructing an image and influencing the visual quality of an image. Computational model for VPMI may be calculated as:

$$VPMI=AIE \cdot \log 2(AG) \cdot LNPF \cdot ACLF \cdot ABWF \quad (16)$$

A principle of this function may be adapted to extract information from the visual scene. The measurement of the features may provide an approximation of subjective perceptual image quality. The estimation VPMI may be a final quality assessment score, and a higher value of VPMI may be a higher quality image.

Figure 22:
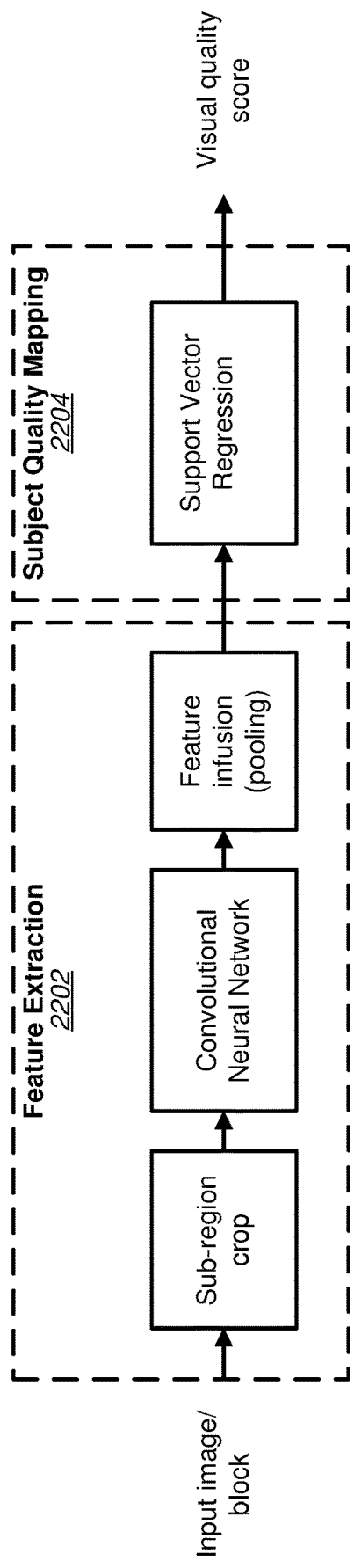
FIG. 22 illustrates an example of no reference image quality assessment based on deep Learning for Blind Image Quality Assessment (DeepBIQ).

FIG. 22 illustrates an example of a no reference image quality assessment based on deep Learning for Blind Image Quality Assessment (DeepBIQ).

At 2202, input image/block may be cropped into a sub-regions. A deep convolutional neural networks (CNN) may receive each sub-region and outputs a features. The output features from each sub-region may be fused by pooling. The pooled features may be inputted to support vector regression (SVR) machine to output the visual quality score. DeepBIQ may use a deep convolutional neural networks (CNN) to classify image crops into five distortion classes (e.g. bad, poor, fair, good, and excellent).

Deep convolutional neural networks (CNNs) may be a class of learnable architectures used in many image domains such as recognition, annotation, retrieval, object detection, etc. CNNs may be composed of several convolutional layers and linear layers of processing, each involving linear as well as non-linear operators that may be jointly learned in an end-to-end manner to solve a particular task. A typical CNN architecture may comprise of a set of stacked layers: convolutional layers to extract local features. The convolutional layers in the CNNs may perform as image filters. The linear layers in the CNNs may perform as matrix product of input image and weighs. DeepBIQ has 5 convolutional layers.

DeepBIQ comprises 3 point-wise non-linear mappings; pooling layers, which aggregates the statistics of the features at nearby locations; and fully connected layers. The result of the last fully connected layer may be the CNN output. CNN architectures may vary in the number of layers, the number of outputs per layer, the size of the convolutional filters, and the size and type of spatial pooling. CNNs may be trained in a supervised manner by means of standard backpropagation.

CNN features may be computed on multiple subregions (e.g. crops) of the input image. Crops dimensions may be chosen to be equal to the CNN input size so that no scaling operation may be involved. In an example, each crop may cover almost 21% of the original image. The use of multiple crops may permit to evaluate the local quality. The final image quality may be computed by pooling the evaluation of each single crop. This may enable distinguishing between a globally blurred image and a high-quality depth-of-field image. The pooling may be used as an information fusion performed on the predicted quality scores. The SVR may predict a quality score for each image crop, and these scores may be fused using a minimum, average, and/or maximum pooling operators.

In an example embodiment, the fine-tuning of a pre-trained CNN may be used for exploiting training data. When the amount of data is small, the training process may keep some of the earlier layers fixed and fine-tune some higher-level portion of the network. This procedure may also be called transfer learning. The first layers of CNNs may learn feature similar to Gabor filters and color blobs that appear not to be specific to a particular image domain; while the following layers of CNNs become progressively more specific to the given domain. Fine-tuning procedure substitutes the last fully connected layer of a pre-trained CNN with a new one initialized with random values. The new layer is trained from scratch, and the weights of the other layers are updated using the back-propagation algorithm with the available data for image quality assessment. In DeepBIQ, image quality data may be a set of images having human average quality scores (e.g. MOS). The CNN may be discriminatively fine-tuned to classify image sub-regions into five classes according to the 5-points MOS scale. The five classes may be obtained by a crisp partition of the MOS: bad (score∈[0, 20]), poor (score∈]20, 40]), fair (score∈]40, 60]), good (score∈]60, 80]), and excellent (score∈]80, 100]). Once the CNN is trained, the CNN may be used for feature extraction, just like one of the pre-trained CNNs At 2204, the output of CNN is used as feature for SVR machine. The SVR may maps the CNN features to the visual quality scores. SVR machine may adopt a linear kernel to learn a mapping function from the CNN features to the perceived quality scores (e.g. MOS).

Figure 23:
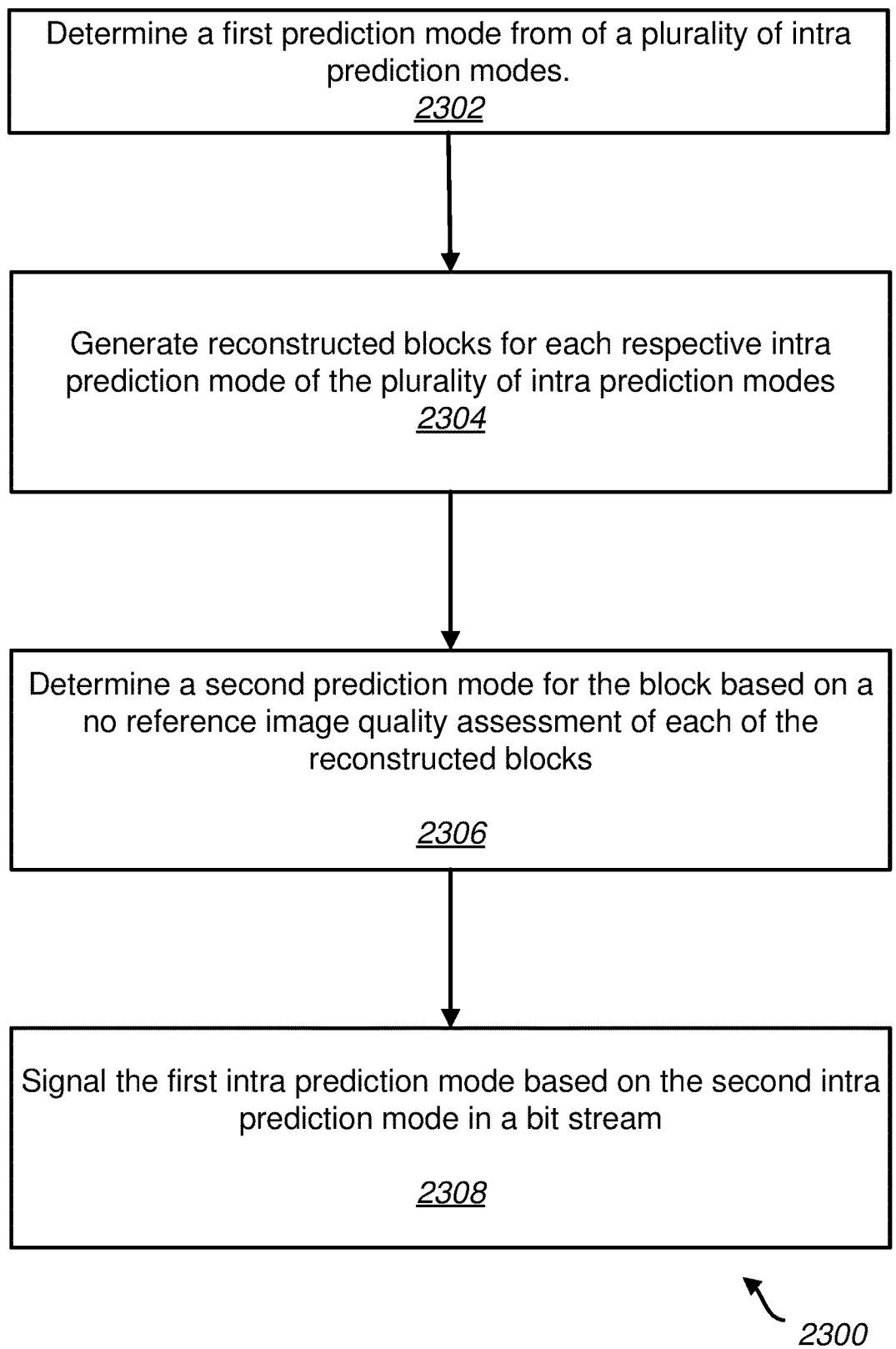
FIG. 23 illustrates a flowchart of a method for block encoding with no reference image quality assessment based decoder side prediction in accordance with embodiments of the present disclosure.

FIG. 23 illustrates a flowchart 2300 of a method for block encoding with a no reference image quality assessment based decoder side intra prediction in accordance with embodiments of the present disclosure. The method of flowchart 2300 may be implemented by an encoder, such as encoder 200 in FIG. 2. The flowchart 2300 starts at 2302.

At 2302, the encoder may determine a first prediction mode from of a plurality of intra prediction modes for a block being encoded. The first prediction mode may be determined based on a rate-distortion cost. For example, an intra prediction mode that shows minimum rate-distortion cost or minimum distortion from the plurality of intra prediction modes may be selected/determined as a first prediction mode for a block being encoded (or current block). The encoder may predict the first prediction mode of the current block from the plurality of intra prediction modes. For example, the encoder may estimate prediction blocks for each of the 35 intra prediction modes in HEVC or 67 intra prediction modes in VVC. For each intra prediction mode applied, the encoder may determine a prediction error for the current block based on a difference (e.g., sum of squared differences (SSD), sum of absolute differences (SAD), or sum of absolute transformed differences (SATD)) between the prediction samples determined for the intra prediction mode and the original samples of the current block. The encoder may select one of the intra prediction modes to encode the current block based on the determined prediction errors as the first prediction mode. For example, the encoder may select an intra prediction mode that results in the smallest prediction error for the current block as the first prediction mode. In an example, the encoder may select an intra prediction mode as the first prediction mode based on a rate-distortion measure (e.g., Lagrangian rate-distortion cost) determined using the prediction errors.

At 2304, a reconstructed block for each respective intra prediction modes may be generated, for example, as explained in FIG. 19. The reconstructed blocks for each respective intra prediction modes may be generated by summation of a prediction block of each respective intra prediction mode and a reconstructed residual block based on the first prediction mode. For example, the encoder may generate a reconstructed block for each respective intra prediction mode of the plurality of intra prediction modes based on a prediction blocks generated for the respective intra prediction modes and/or a reconstructed residual block based on the first prediction mode. In an example, generating the prediction blocks comprises generating different prediction blocks for each intra prediction mode of the plurality of intra prediction modes.

The encoder may generate the prediction blocks of each respective intra prediction modes. For example, the encoder may generate the prediction blocks for each of the 35 intra prediction modes in HEVC or 67 intra prediction modes in VVC. A residual block may be difference between the current block and the prediction block based on the first prediction mode.

The encoder may generate the reconstructed residual block of the first prediction mode by encoding and decoding the residual block. The encoder may encode the residual block by applying transform the residual block to generate transform coefficients; and quantization of the transform coefficients; de-quantizing the inverse transformed transform coefficients; and/or inverse transforming of the transform coefficients. For example, the encoded result of the residual block may be the transform coefficients. The transform coefficients may be decoded into the reconstructed residual block by de-quantization and inverse transforming of the transform coefficients.

At 2306, visual qualities of reconstructed blocks for each respective intra prediction modes may be measured/determined by the no reference image quality assessment. A second prediction mode may be determined, from the plurality of intra prediction modes, for the block based on visual quality of each of the reconstructed blocks.

From the plurality of the intra prediction modes, the intra prediction mode that shows a determined visual quality value from the plurality of the intra prediction modes may be selected as a second prediction mode. For example, the determined visual quality value may be the maximum visual quality value among the visual qualities of the respective reconstructed blocks. The second prediction mode for the block may be determined based on the visual quality, among the visual qualities of the reconstructed blocks, with a highest visual quality. The visual quality of each of the reconstructed blocks may be determined without using the block as a reference. For example, visual quality of each of the reconstructed blocks may be determined based on a visual parameter measurement index (VPMI). For example, the visual quality of each of the reconstructed blocks may be determined based on a deep learning for blind image quality assessment (DeepBIQ).

The no reference image quality assessment may be a method of determining a visual quality without using a reference image or reference image. The determining the second prediction mode with the no reference image quality assessment may be performed in both the encoder and decoder. The encoder may not signal intra prediction mode to decoder. The no reference image quality assessment may generate a visual quality metric without using reference image or reference image block. Based on a trained prediction model, the no reference image quality assessment may predict the visual quality of the input image or input image block. For example, the no reference image quality assessment may be visual parameter measurement index (VPMI). For example, the no reference image quality assessment may be deep Learning for Blind Image Quality Assessment (DeepBIQ).

At 2308, the first prediction mode may be signaled based on the second prediction mode in the bit stream. The signaling may comprise signaling, in the bit stream, the first prediction mode according to a syntax structure. For example, the syntax structure may comprise a syntax element, the syntax element indicating the first prediction mode. For example, an occurrence of the syntax element in the syntax structure may be conditioned based on a decoder-side-prediction. For example, a value of the decoder-side-prediction may be determined based on whether the first prediction mode is the same as the second prediction mode.

If the first prediction mode is equal to the second prediction mode, an enabled decoder-side-prediction may be signaled instead of signaling the first prediction mode. For example, signaling an intra prediction mode that may require 6 bits (35 modes) in HEVC, 8 bits in VVC (67 modes) may be reduced into 1 bit in this case.

For example, if the first prediction mode is not equal to the second prediction mode, the first prediction mode may be signaled following signaling the disabled decoder-side-prediction.

Figure 24:
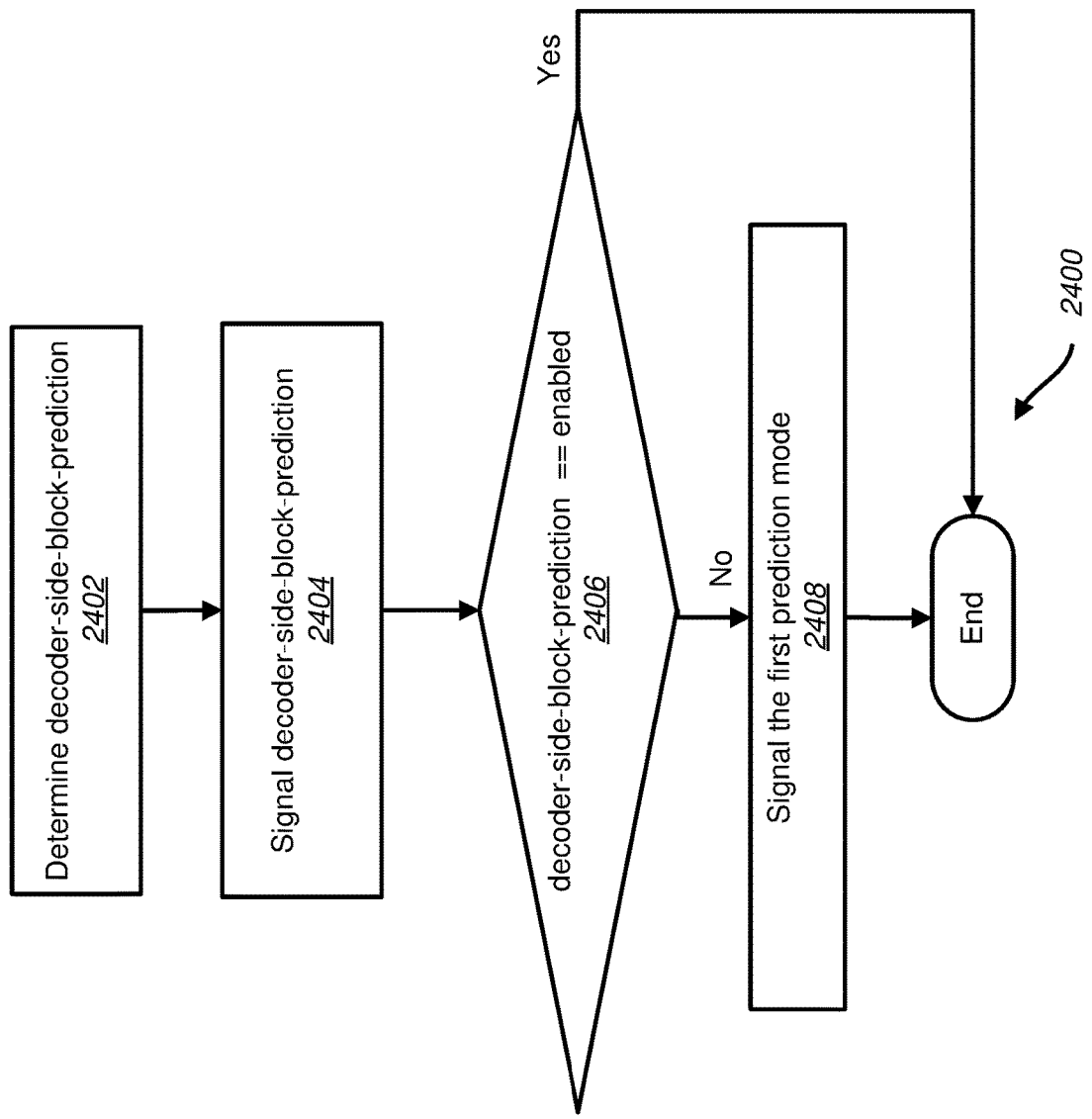
FIG. 24 illustrates a flowchart of a method for signaling no reference image quality assessment based decoder side prediction.

FIG. 24 illustrates a flowchart 2400 of a method for signaling a no reference image quality assessment based decoder side prediction, which explains 2308 in more detail. The method of flowchart 2400 begins at 2402.

At 2402, a value of a decoder-side-prediction may be determined based on the first prediction mode and the second prediction mode. If the first prediction mode is equal to the second prediction mode, the decoder-side-prediction may be enabled. If the first prediction mode is not equal to the second prediction mode, the decoder-side-prediction may be disabled.

At 2404, the decoder-side-prediction may be signaled to decoder in accordance with lossless entropy coding. Context-based adaptive variable length coding (CAVLC) may be entropy coding method employed in the H.264/AVC standard. Context-based adaptive binary arithmetic coding (CABAC) is employed in H.264/AVC, HEVC, and VVC.

At 2406, the decoder-side-prediction may be checked. If the decoder-side-prediction is disabled, the first prediction mode may be signaled to decoder in accordance with lossless entropy coding at 2408. If the decoder-side-prediction is enabled, the first prediction mode may not be signaled. By reducing the amount of data for signaling intra prediction mode, compression efficiency may be enhanced.

Figure 25:
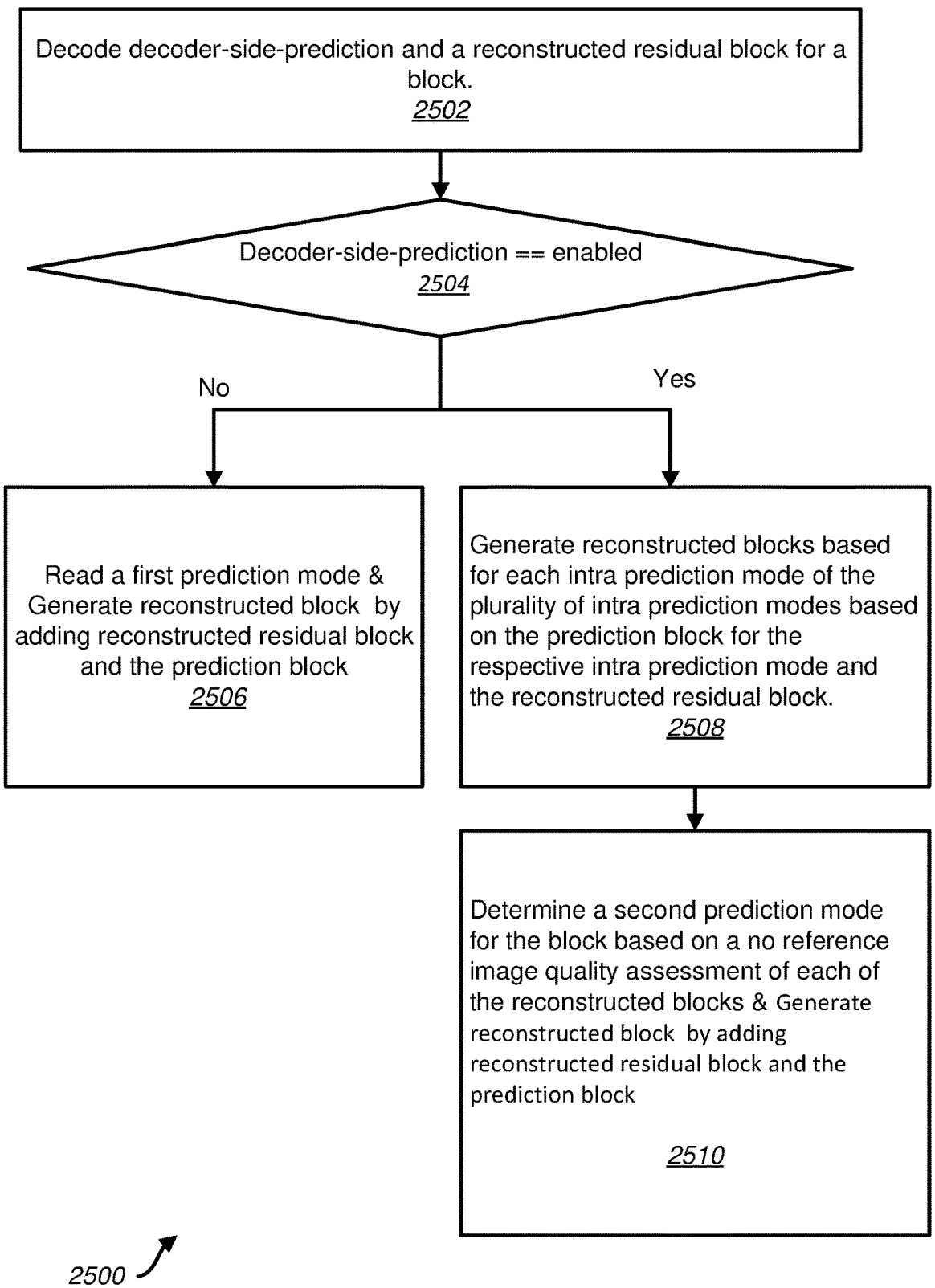
FIG. 25 illustrates a flowchart of a method for block decoding with no reference image quality assessment based decoder side prediction in accordance with embodiments of the present disclosure.

FIG. 25 illustrates a flowchart 2500 of a method for block decoding with a no reference image quality assessment based decoder side prediction in accordance with embodiments of the present disclosure. The method of flowchart 2500 begins at 2502.

At 2502, decoder-side-prediction and a reconstructed residual block for a block being decoded (or current block) may be decoded. The decoder may read decoder-side-prediction and transform coefficients of the current block from a bit stream containing the encoded current block. The decoder may reconstruct (or decode) the decoder-side-prediction and the transform coefficients by applying entropy decoding to the corresponding bits in the bit stream.

The decoder may generate the reconstructed residual block by performing de-quantization and inverse transformation of the transform coefficients of the current block, for example, as explained at 1804. For example, the decoding the transform coefficients into reconstructed may comprise de-quantization of the transformed coefficients and/or inverse transform for de-quantized transform coefficients generating the residual block.

At 2504, the block may be decoded based on the decoder-side-prediction. For example, the decoder-side-prediction decoded at 2502 may be checked. If decoder-side-prediction is disabled, 2506 is performed. If decoder-side-prediction is enabled, 2508 is performed. A reconstructed block is decoded (reconstructed) samples of the current block. If the decoder-side-prediction is disabled, the reconstructed block may be generated at 2506. If decoder-side-prediction is enabled, the reconstructed block may be generated at 2510.

At 2506, based on the decoder-side-prediction disabled, the decoding a block may comprise receiving a first prediction mode from bit stream, generating a prediction block based on the first prediction mode, and generating a reconstructed block for the block by summation of the prediction block and the reconstructed residual block.

For example, the decoder may read the first prediction mode of the current block from the bit stream by reading and performing entropy decoding the corresponding bits from the bit stream containing the encoded current block.

The decoder may generate a prediction block based on the first prediction mode. The prediction block may be predicted samples of the current block using intra prediction based on the first prediction mode. For example, generation of prediction block according to each intra prediction mode is explained above.

A reconstructed block may be generated by summation of the prediction block based on the first prediction mode and the reconstructed residual block. The reconstructed block may be decoded (reconstructed) samples of the current block. For example, the reconstructed block may be generated by summation of the prediction block and the reconstructed residual block.

At 2508, the decoder may generate a reconstructed block for each respective intra prediction modes, for example, as explained in FIG. 19. Based on the decoder-side-prediction enabled, generating the reconstructed blocks comprises generating a prediction block for each respective intra prediction mode, generating a reconstructed block for each respective intra prediction mode by summation of the prediction blocks for each respective intra prediction mode and the reconstructed residual block, and determining a reconstructed block for the block from the plurality of the reconstructed blocks based on a no reference image quality assessment. A reconstructed block for each respective intra prediction mode of the plurality of intra prediction modes may be generated based on prediction blocks generated for the respective intra prediction modes and a reconstructed residual block based on the first prediction mode. In an example, the reconstructed blocks for each respective intra prediction modes may be generated by summation of the prediction blocks of each respective intra prediction mode and the reconstructed residual block.

The decoder may predict the prediction blocks of each respective intra prediction modes. For example, the encoder may generate the prediction blocks for each of the 35 intra prediction modes in HEVC or 67 intra prediction modes in VVC.

At 2510, a second prediction mode, of the plurality of intra prediction modes, for the block may be determined based on a visual quality of each of the reconstructed blocks.

The second prediction mode for the block may be determined based on the visual quality, among the visual qualities of the reconstructed blocks, with a highest visual quality. The visual quality of each of the reconstructed blocks may be determined without using the block as a reference. For example, visual quality of each of the reconstructed blocks may be determined based on a visual parameter measurement index (VPMI). For example, the visual quality of each of the reconstructed blocks may be determined based on a deep learning for blind image quality assessment (DeepBIQ).

For example, a second prediction mode may be determined a reconstructed block for the block from the plurality of the reconstructed blocks based on the prediction of intra prediction mode with the no reference image quality assessment that results in a highest visual quality value for the reconstructed block of the intra prediction mode. The no reference image quality assessment may be a method of determining a visual quality without using a reference image or reference image. The decoder may generate a reconstructed block based on the second prediction mode. For example, the no reference image quality assessment is visual quality metric without an original image. For example, the no reference image quality assessment may be visual parameter measurement index (VPMI). For example, the no reference image quality assessment may be deep Learning for Blind Image Quality Assessment (DeepBIQ).

For example, the prediction of intra prediction mode with the no reference image quality assessment is explained in FIG. 19.

In the prediction of intra prediction mode with the no reference image quality assessment, visual qualities of the reconstructed blocks for each respective intra prediction modes may be measured by the no reference image assessment. From the plurality of the intra prediction modes, the intra prediction mode that shows a determined visual quality by the no reference image quality assessment may be selected as the second prediction mode. For example, the determined visual quality value may be the maximum visual quality value among the plurality of intra prediction modes.

The no reference image quality assessment may generate a visual quality metric without an original image. Based on a trained prediction model, the no reference image quality assessment may predict the visual quality of the input image/block.

The decoder may generate a prediction block based on the second prediction mode. The prediction block may be predicted samples of the current block using intra prediction based on the second prediction mode. For example, generation of prediction block according to each intra prediction mode may be explained above.

The reconstructed block may be generated by summation of the prediction block based on the second prediction mode and the reconstructed residual block.

Figure 26:
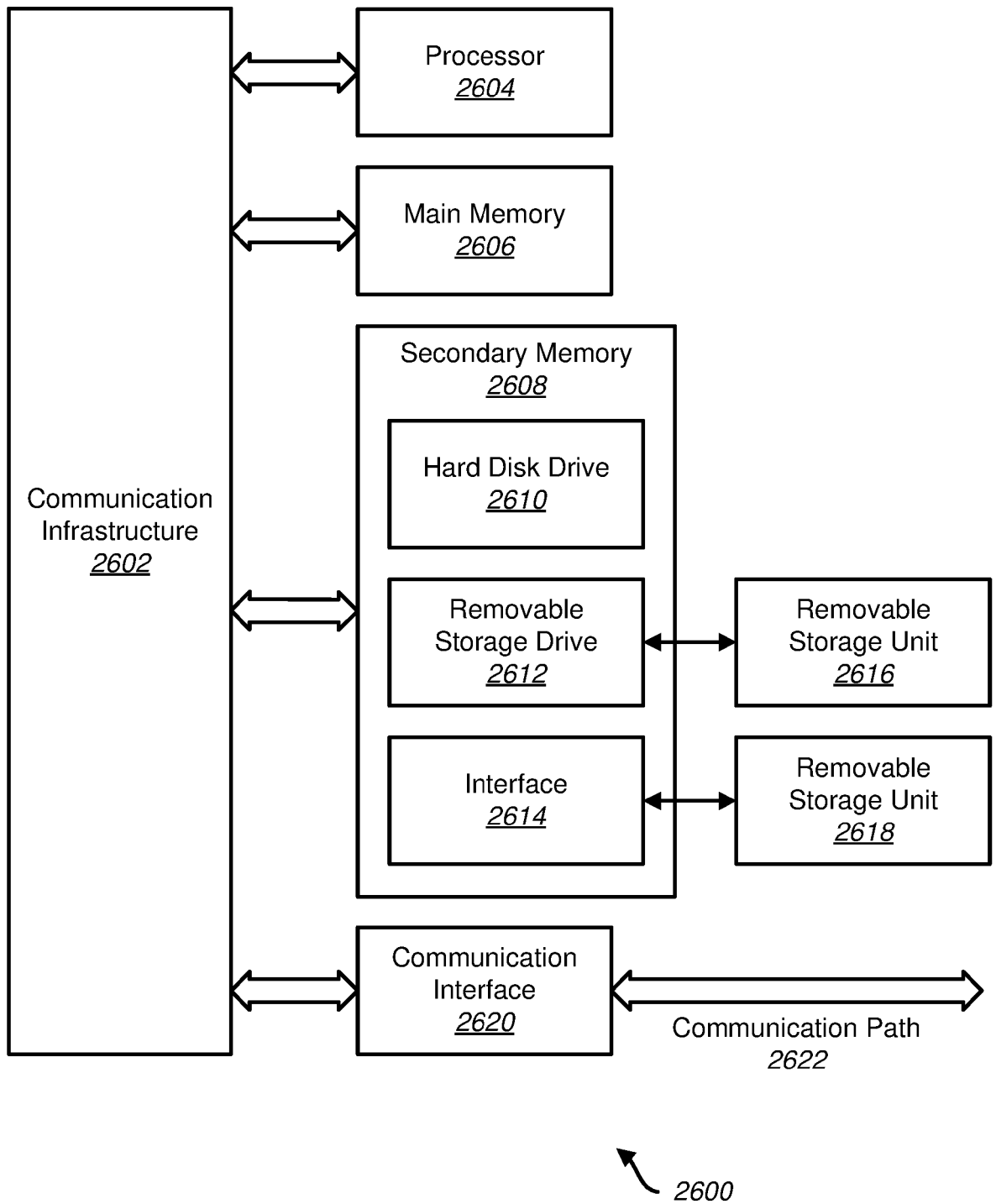
FIG. 26 illustrates a block diagram of an example computer system in which embodiments of the present disclosure may be implemented.

Embodiments of the present disclosure may be implemented in hardware using analog and/or digital circuits, in software, through the execution of instructions by one or more general purpose or special-purpose processors, or as a combination of hardware and software. Consequently, embodiments of the disclosure may be implemented in the environment of a computer system or other processing system. An example of such a computer system 2600 is shown in FIG. 26. Blocks depicted in the figures above, such as the blocks in FIGS. 1, 2, and 3, may execute on one or more computer systems 2600. Furthermore, each of the steps of the flowcharts depicted in this disclosure may be implemented on one or more computer systems 2600.

Computer system 2600 includes one or more processors, such as processor 2604. Processor 2604 may be, for example, a special purpose processor, general purpose processor, microprocessor, or digital signal processor. Processor 2604 may be connected to a communication infrastructure 902 (for example, a bus or network). Computer system 2600 may also include a main memory 2606, such as random access memory (RAM), and may also include a secondary memory 2608.

Secondary memory 2608 may include, for example, a hard disk drive 2610 and/or a removable storage drive 2612, representing a magnetic tape drive, an optical disk drive, or the like. Removable storage drive 2612 may read from and/or write to a removable storage unit 2616 in a well-known manner. Removable storage unit 2616 represents a magnetic tape, optical disk, or the like, which is read by and written to by removable storage drive 2612. As will be appreciated by persons skilled in the relevant art(s), removable storage unit 2616 includes a computer usable storage medium having stored therein computer software and/or data.

In alternative implementations, secondary memory 2608 may include other similar means for allowing computer programs or other instructions to be loaded into computer system 2600. Such means may include, for example, a removable storage unit 2618 and an interface 2614. Examples of such means may include a program cartridge and cartridge interface (such as that found in video game devices), a removable memory chip (such as an EPROM or PROM) and associated socket, a thumb drive and USB port, and other removable storage units 2618 and interfaces 2614 which allow software and data to be transferred from removable storage unit 2618 to computer system 2600.

Computer system 2600 may also include a communications interface 2620. Communications interface 2620 allows software and data to be transferred between computer system 2600 and external devices. Examples of communications interface 2620 may include a modem, a network interface (such as an Ethernet card), a communications port, etc. Software and data transferred via communications interface 2620 are in the form of signals which may be electronic, electromagnetic, optical, or other signals capable of being received by communications interface 2620. These signals are provided to communications interface 2620 via a communications path 2622. Communications path 2622 carries signals and may be implemented using wire or cable, fiber optics, a phone line, a cellular phone link, an RF link, and other communications channels.

As used herein, the terms "computer program medium" and "computer readable medium" are used to refer to tangible storage media, such as removable storage units 2616 and 2618 or a hard disk installed in hard disk drive 2610. These computer program products are means for providing software to computer system 2600. Computer programs (also called computer control logic) may be stored in main memory 2606 and/or secondary memory 2608. Computer programs may also be received via communications interface 2620. Such computer programs, when executed, enable the computer system 2600 to implement the present disclosure as discussed herein. In particular, the computer programs, when executed, enable processor 2604 to implement the processes of the present disclosure, such as any of the methods described herein. Accordingly, such computer programs represent controllers of the computer system 2600.

In another embodiment, features of the disclosure may be implemented in hardware using, for example, hardware components such as application-specific integrated circuits (ASICs) and gate arrays. Implementation of a hardware state machine to perform the functions described herein will also be apparent to persons skilled in the relevant art(s).

What is claimed is:

1. A method comprising:
   receiving, by a decoder, from a bitstream for a block:
      an indication of decoder-side-prediction of an intra prediction mode, wherein a first value of the indication indicates that the intra prediction mode is to be determined by the decoder and a second value of the indication indicates that the intra prediction mode is to be determined from the bitstream; and
      a reconstructed residual block;
   based on the indication having the first value,
      generating, by the decoder, a plurality of reconstructed blocks for a plurality of intra prediction modes, wherein each reconstructed block of the plurality of reconstructed blocks is generated based on:
         a prediction block generated for a respective intra prediction mode of the plurality of intra prediction modes; and
         the reconstructed residual block;
      selecting, by the decoder, a prediction mode, from the plurality of intra prediction modes, as the intra prediction mode of the block based on
         a visual quality of each of the plurality of reconstructed blocks; and
   decoding, by the decoder, the block based on the intra prediction mode.

2. The method of claim 1, wherein the receiving comprises:
   receiving transform coefficients from the bitstream; and
   decoding the transform coefficients to generate the reconstructed residual block.

3. The method of claim 2, wherein the decoding the transform coefficients to generate the reconstructed residual block comprises:
   de-quantizing the transform coefficients; and
   inverse transforming the de-quantized transform coefficients.

4. The method of claim 1, wherein the prediction mode for the block is selected further based on the visual quality, among the visual qualities of the reconstructed blocks, with a highest visual quality.

5. The method of claim 1, wherein the visual quality of each of the reconstructed blocks is determined without using the block as a reference.

6. The method of claim 1, wherein the reconstructed block, generated for each respective intra prediction mode of the plurality of intra prediction modes, is generated by summing the prediction block generated for the respective intra prediction mode and the reconstructed residual block.

7. The method of claim 1, wherein the visual quality of each of the reconstructed blocks is determined based on a visual parameter measurement index.

8. The method of claim 1, wherein the visual quality of each of the reconstructed blocks is determined based on a deep Learning for Blind Image Quality Assessment.

9. A decoder comprising:
   one or more processors; and
   memory storing instructions that, when executed by the one or more processors, cause the decoder to:
      receive, from a bitstream for a block:
         an indication of decoder-side-prediction of an intra prediction mode, wherein a first value of the indication indicates that the intra prediction mode is to be determined by the decoder and a second value of the indication indicates that the intra prediction mode is to be determined from the bitstream; and
         a reconstructed residual block;
      based on the indication having the first value,
         generate a plurality of reconstructed blocks for a plurality of intra prediction modes, wherein each reconstructed block of the plurality of reconstructed blocks is generated based on:
            a prediction block generated for a respective intra prediction mode of the plurality of intra prediction modes; and
            the reconstructed residual block;
         select, by the decoder, a prediction mode, from the plurality of intra prediction modes, as the intra prediction mode of the block based on
            a visual quality of each of the plurality of reconstructed blocks; and
      decode the block based on the intra prediction mode.

10. The decoder of claim 9, wherein to receive the reconstructed residual block, the decoder is further caused to:
   receive transform coefficients from the bitstream; and
   decode the transform coefficients to generate the reconstructed residual block.

11. The decoder of claim 10, wherein to decode the transform coefficients, the decoder is further caused to:
   de-quantize the transform coefficients; and
   inverse transform the de-quantized transform coefficients.

12. The decoder of claim 9, wherein the prediction mode for the block is selected further based on the visual quality, among the visual qualities of the reconstructed blocks, with a highest visual quality.

13. The decoder of claim 9, wherein the visual quality of each of the reconstructed blocks is determined without using the block as a reference.

14. The decoder of claim 9, wherein the reconstructed block, generated for each respective intra prediction mode of the plurality of intra prediction modes, is generated by summing the prediction block generated for the respective intra prediction mode and the reconstructed residual block.

15. The decoder of claim 9, wherein the visual quality of each of the reconstructed blocks is determined based on a visual parameter measurement index.

16. The decoder of claim 9, wherein the visual quality of each of the reconstructed blocks is determined based on a deep Learning for Blind Image Quality Assessment.

17. A non-transitory computer-readable medium storing instructions that, when executed by one or more processors of a decoder, cause the decoder to:
   receive, from a bitstream for a block:
      an indication of decoder-side-prediction of an intra prediction mode, wherein a first value of the indication indicates that the intra prediction mode is to be determined by the decoder and a second value of the indication indicates that the intra prediction mode is to be determined from the bitstream; and
      a reconstructed residual block;
   based on the indication having the first value,
      generate a plurality of reconstructed blocks for a plurality of intra prediction modes, wherein each reconstructed block of the plurality of reconstructed blocks is generated based on:
         a prediction block generated for a respective intra prediction mode of the plurality of intra prediction modes; and
         the reconstructed residual block;
      select a prediction mode, from the plurality of intra prediction modes, as the intra prediction mode of the block based on
         a visual quality of each of the plurality of reconstructed blocks; and
   decode the block based on the intra prediction mode.

18. The non-transitory computer-readable medium of claim 17, wherein the prediction mode for the block is selected further based on the visual quality, among the visual qualities of the reconstructed blocks, with a highest visual quality.

19. The non-transitory computer-readable medium of claim 17, wherein the visual quality of each of the reconstructed blocks is determined without using the block as a reference.

20. The non-transitory computer-readable medium of claim 17, wherein the reconstructed block, generated for each respective intra prediction mode of the plurality of intra prediction modes, is generated by summing the prediction block generated for the respective intra prediction mode and the reconstructed residual block.

* * * * *